(12) United States Patent
Bryan

(10) Patent No.: US 10,471,109 B2
(45) Date of Patent: Nov. 12, 2019

(54) COMPOSITIONS AND METHODS FOR PROMOTING NITRIC OXIDE PRODUCTION THROUGH AN ORAL DELIVERY SYSTEM

(71) Applicant: BOARD OF REGENTS, THE UNIVERSITY OF TEXAS SYSTEM, Austin, TX (US)

(72) Inventor: Nathan S. Bryan, Austin, TX (US)

(73) Assignee: The Board of Regents of The University of Texas System, Austin, TX (US)

(*) Notice: Subject to any disclaimer, the term of this patent is extended or adjusted under 35 U.S.C. 154(b) by 237 days.

(21) Appl. No.: 14/903,242

(22) PCT Filed: May 5, 2014

(86) PCT No.: PCT/US2014/036849
§ 371 (c)(1),
(2) Date: Jan. 6, 2016

(87) PCT Pub. No.: WO2014/182632
PCT Pub. Date: Nov. 13, 2014

(65) Prior Publication Data
US 2016/0151428 A1    Jun. 2, 2016

Related U.S. Application Data

(60) Provisional application No. 61/819,567, filed on May 4, 2013.

(51) Int. Cl.
*A61K 35/741* (2015.01)
*A61K 35/74* (2015.01)

(52) U.S. Cl.
CPC ........... *A61K 35/741* (2013.01); *A61K 35/74* (2013.01)

(58) Field of Classification Search
CPC .. A61K 49/0019; A61K 31/65; A61K 35/742; A61K 35/74; A61K 35/741; A61K 35/744; A61K 9/0053; A61K 35/745; A61K 35/747; A61K 45/06; A61K 9/4816; A61K 2035/115; A61K 31/7004; A61K 31/7016; A61K 31/715; A61K 35/39; A61K 38/46; A61K 2300/00; A61K 49/0058; A61K 38/40; A61K 2039/52; A61K 2039/54; A61K 2039/545; A61K 2039/55544; A61K 2039/577; A61K 2039/58; A61K 39/35; A61K 39/02; A61K 49/0004; A61K 2800/57; A61K 47/51; A61K 8/64; A61K 2800/5922; A61K 2800/594; A61K 2800/87; A61K 2800/884; A61K 2800/92; A61K 31/702; A61K 31/716; A61K 31/733; A61K 8/60; A61K 8/73; A61K 8/99; A61K 9/0034; A61K 9/0043; A61K 9/006; A61B 2010/0061; A61B 2562/0233; A61B 5/0071; A61B 5/073; A61B 5/14503; A61B 5/14539; A61B 5/14546; A61B 5/4238; A61B 5/4255; A61B 5/6861; A61B 10/0038; A61B 10/0045; A61B 2010/0074; A61B 5/0084; A61B 5/01; A61B 5/036; A61B 5/14552; A61B 5/42; A61B 1/00009; A61B 1/041; A61B 1/043; A61B 2034/2065; A61B 2560/0233; A61B 2560/0242; A61B 2560/0247; A61B 2560/0252; A61B 2560/0475; A61B 2562/046; A61B 5/002; A61B 5/0075; A61B 5/024; A61B 5/0531; A61B 5/065; A61B 5/1126; A61B 5/14507; A61B 5/14535; A61B 5/14542; A61B 5/1455; A61B 5/14556; A61B 5/1459; A61B 5/4222; A61B 5/4845; A61B 5/4848; A61B 5/4866; A61B 5/6873; A61B 5/6898;

(Continued)

(56) References Cited

U.S. PATENT DOCUMENTS

| | | | |
|---|---|---|---|
| 8,303,995 B1 | 11/2012 | Bryan et al. | 424/718 |
| 2009/0324547 A1* | 12/2009 | Wikstrom | A61K 8/19 424/93.2 |
| 2010/0092441 A1 | 4/2010 | Lundberg et al. | 424/93.45 |
| 2011/0081699 A1 | 4/2011 | Hugenholtz et al. | 435/168 |
| 2012/0321724 A1 | 12/2012 | Bryan et al. | 424/718 |
| 2013/0071371 A1 | 3/2013 | Bryan et al. | 424/94.4 |

FOREIGN PATENT DOCUMENTS

| | | |
|---|---|---|
| WO | WO/02/07741 | 1/2002 |
| WO | WO/02/13982 | 2/2002 |
| WO | WO/09/09163 | 1/2009 |

OTHER PUBLICATIONS

Cole et al., "Biochemical and genetic characterization of nirB mutants of *Escherichia coli* K 12 pleiotropically defective in nitrite and sulphite reduction", *J Gen Microbiol.*, 120(2): 475-483, 1980.

(Continued)

*Primary Examiner* — Deborah K Ware
(74) *Attorney, Agent, or Firm* — Norton Rose Fulbright US LLP

(57) ABSTRACT

Probiotic compositions, particularly oral compositions, comprising one or more bacteria that are capable of producing nitrite and/or nitric oxide in a subject are provided. Some compositions further comprise nitrate/nitrate, such as a botanical source of nitrate. Some compositions further comprise botanical sources of nitrate reductase. Also, provided are methods of improving the oral and/or vascular health of a subject by orally administering a composition comprising one or more bacteria capable of producing nitric oxide. Methods of repopulating the nitric oxide producing microflora and bacterial environment in the oral cavity of a subject are also provided.

14 Claims, 5 Drawing Sheets

(58) Field of Classification Search
CPC ... A61B 5/7257; A61B 5/7275; A61B 5/7282; A61B 5/742; C12M 29/26; C12M 23/34; C12M 29/04; C12M 41/34; C12N 1/20; C12N 11/02; C12N 5/0679; C12N 15/74; C12N 15/902; C12Q 1/045; C12Q 1/06; C12Q 1/10; G01N 1/10; G01N 1/20; G01N 1/38; G01N 2001/1031; G01N 21/76; G01N 33/4833; G01N 33/487; G01N 33/582; G01N 2333/52; G01N 33/6863; A61M 31/005; C07K 14/79; A23L 33/135; A23L 3/34635; A23L 3/3571; A23V 2002/00; A61F 5/0003; Y02A 50/469; Y02A 50/481; Y02A 50/491; Y02A 50/473; Y02A 90/26; A23B 4/22; A61Q 11/00; A61Q 17/005; A61Q 19/00; A61Q 5/02; G16B 50/00; G16B 20/00; G16B 20/40; G16B 30/10; G16B 40/00; G16B 40/20; G16B 40/30; G16H 10/40; G16H 50/20; G16H 20/60; A61P 11/02; A61P 15/02; A61P 1/02; A61P 31/04

See application file for complete search history.

(56) References Cited

OTHER PUBLICATIONS

Dewhirst et al., "The human oral microbiome" *J Bacteriol*, 192(19): 5002-5017, 2010.

Hyde et al., "Metagenomic analysis of nitrate-reducing bacteria in the oral cavity: implications for nitric oxide homeostasis", *PLoS One.*, 9(3): e88645, 2014.

International Search Report and Written Opinion issued in PCT/US2014/036849, dated Sep. 15, 2014.

Schreiber et al., "Denitrification in human dental plaque", *BMC Biol.*, 8(24): 1-11, 2010.

Archer, "Evidence that Ingested Nitrate and Nitrite are Beneficial to Health" J Food Protection. 65(5):872-5, 2002.

Duncan, et al., "Chemical Generation of Nitric Oxide in the Mouth from the Enterosalivary circulation of dietary nitrate" Nature Med. 1(6):546-551, 1995.

Extended European Search Report in European Application No. 14794420.1 dated Nov. 28, 2016.

\* cited by examiner

COMPOSITIONS AND METHODS FOR PROMOTING NITRIC OXIDE PRODUCTION THROUGH AN ORAL DELIVERY SYSTEM

CROSS-REFERENCE TO RELATED APPLICATIONS

This application is a national phase application under 35 U.S.C. § 371 of International Application No. PCT/US2014/036849 filed May 5, 2014, which claims priority to U.S. Provisional Patent Application No. 61/819,567, filed May 4, 2013. The entire contents of each of the above-referenced disclosures are specifically incorporated herein by reference without disclaimer.

BACKGROUND OF THE INVENTION

A. Field of the Invention

The invention relates to compositions and methods for enhancing nitric oxide production in the oral cavity and more specifically to compositions and methods for enhancing nitric oxide production that comprise probiotics.

B. Description of Related Art

The human gastrointestinal tract represents a major habitat for bacterial colonization. For example, the microbiota of the lower intestinal tract is widely recognized to play a symbiotic role in maintaining a healthy host physiology by participating in nutrient acquisition and bile acid recycling, among other activities. Another region where microbiota can be found is in the oral cavity.

While, the role of upper gastrointestinal tract microbiota in disease is well studied, specific contributions to host health are not well defined. One potential symbiotic relationship between oral bacteria and humans is via the entero-salivary nitrate-nitrite-nitric oxide pathway, which can positively affect nitric oxide (NO) production and homeostasis. (Lundberg, Weitzberg et al. 2004; Lundberg, Weitzberg et al. 2008).

The gaseous free radical NO, which is endogenously produced in vascular endothelial cells, neurons and immune cells, plays a critical role in various physiological processes, including vascular homeostasis, neurotransmission, and host defense mechanisms, respectively. Continuous availability of NO is essential for cardiovascular system integrity. In the circulation, NO is an important regulator of vascular tone and blood pressure, and inhibits oxidative stress, platelet aggregation, and leukocyte adhesion (Moncada, Palmer et al. 1991). NO insufficiency is strongly correlated with cardiovascular risk factors (Kleinbongard, Dejam et al. 2006), is causal for endothelial dysfunction, and serves as a profound predictive factor for future atherosclerotic disease progression (Schachinger, Britten et al. 2000; Halcox 2002; Bugiardini, Manfrini et al. 2004; Lerman and Zeiher 2005) and cardiovascular events (Yeboah, Crouse et al. 2007; Yeboah, Folsom et al. 2009). In mammalian systems, NO is generated by NO synthases (NOS) from the amino acid L-arginine and molecular oxygen (Moncada and Higgs 1993). The entero-salivary nitrate-nitrite-NO pathway is a NOS-independent and oxygen-independent pathway to NO formation that is an important alternative pathway to produce bioactive NO, particularly during periods of hypoxia (Lundberg, Weitzberg et al. 2004; Doel, Benjamin et al. 2005; Bryan, Calvert et al. 2008).

Dietary nitrate, obtained primarily from green leafy vegetables and beets, is rapidly absorbed from the upper gastrointestinal tract into the bloodstream, where it mixes with the nitrate formed from the oxidation of endogenous NO produced from mammalian NOS. Up to 25% of this nitrate is actively taken up by the salivary glands and concentrated up to 20-fold, reaching concentrations approaching 10 mM in the saliva (Lundberg and Govoni 2004). Salivary nitrate is metabolized to nitrite via a two-electron reduction, a reaction that mammalian cells are unable to perform, during anaerobic respiration by nitrate reductases produced by facultative and obligate anaerobic commensal oral bacteria (Duncan, Dougall et al. 1995; Lundberg, Weitzberg et al. 2004). Numerous studies have shown that nitrite produced from bacterial nitrate reduction is an important storage pool for NO in blood and tissues when NOS-mediated NO production is insufficient (Bryan, Calvert et al. 2007; Bryan, Calvert et al. 2008; Webb, Patel et al. 2008; Carlstrom, Larsen et al. 2010; Carlstrom, Persson et al. 2011). In various animal models and in humans, dietary nitrate supplementation has shown numerous beneficial effects, including a reduction in blood pressure, protection against ischemia-reperfusion damage, restoration of NO homeostasis with associated cardioprotection, increased vascular regeneration after chronic ischemia, and a reversal of vascular dysfunction in the elderly (Webb, Bond et al. 2004; Petersson, Carlstrom et al. 2009). Some of these benefits were reduced or completely prevented when the oral microbiota were abolished with an antiseptic mouthwash (Petersson, Carlstrom et al. 2009; Hendgen-Cotta, Luedike et al. 2012) Additionally, it was recently shown that in the absence of any dietary modifications, a seven-day period of antiseptic mouthwash treatment to disrupt the oral microbiota reduced both oral and plasma nitrite levels in healthy human volunteers, and was associated with a sustained increase in both systolic and diastolic blood pressure (Kapil, Haydar et al. 2013). There may be a role for oral nitrate-reducing bacteria in making a physiologically relevant contribution to host nitrite and thus NO levels, with measureable physiological effects, and therefore, there is a need for these types of bacteria.

SUMMARY OF THE INVENTION

The present disclosure relates to compositions and methods for enhancing nitrate reduction activity in the gastrointestinal tract and particularly in the oral cavity. One aspect of the disclosure relates to a probiotic composition comprising: a bacteria isolate or mixture that comprises one or more of *Neisseria, Veillonella, Haemophilus, Actinomyces, Granulicatella, Prevotella, Leptotrichia, Brevibacillus, Porphyromonas, Fusobacterium*, and oral bacteria of the Gemellaceae family, wherein the composition does not contain a contaminating amount of *Lactobacillus*. Such compositions can be oral compositions.

Another aspect of the present disclosure relates to a probiotic composition comprising: a bacteria isolate or mixture consisting essentially of nitrite-accumulating bacteria, where the nitrite-accumulating bacteria are bacteria that allow nitrite levels in a bacteria culture to increase and nitrate levels to decrease when the bacteria culture comprises nitrate and a bacteria isolate or mixture consisting essentially of the nitrite-accumulating bacteria. Such compositions can be oral compositions.

Probiotic composition of the present disclosure can be used for the enhancement of nitric oxide (NO) production in subjects suffering from one or more of cardiovascular disease, atherosclerosis, stroke, ischemic injury, peripheral artery disease, congestive heart failure, hypertension, pulmonary arterial hypertension, hypertension associated with urea cycle disorders and pre-eclampsia, vascular dementia, Alzheimers Disease, metabolic syndrome and type 2 diabetes. Probiotic composition of the present disclosure can be used to treat one or more of the above-listed conditions. In certain embodiments, method of treating a subject, such as a human patient, are provided. The subject may have symptoms of or may have been diagnosed with atherosclerosis, stroke, ischemic injury, peripheral artery disease, congestive heart failure, hypertension, pulmonary arterial hypertension, hypertension associated with urea cycle disorders and preeclampsia, vascular dementia, Alzheimers Disease, metabolic syndrome or type 2 diabetes.

Another aspect of the disclosure relates to methods of using the probiotic compositions of the present disclosure to establish or enhance a bacteria population in the oral cavity or enhance nitrate reduction in the oral cavity of a subject. For example, some embodiments can comprise establishing or enhancing a bacteria population in the oral cavity by administering a probiotic composition, where the probiotic composition comprises bacteria selected from a group consisting essentially of *Neisseria, Veillonella, Haemophilus, Actinomyces, Granulicatella, Prevotella, Leptotrichia, Brevibacillus, Porphyromonas, Fusobacterium*, and clade Gemellaceae, where the composition is configured to release at least a portion of the bacteria in the oral cavity. Other embodiments can comprise enhancing nitrate reduction in the oral cavity by administering or ingesting a probiotic composition, where the probiotic composition comprises a bacteria isolate or mixture consisting essentially of nitrite-accumulating bacteria, where the nitrite-accumulating bacteria are bacteria that allow nitrite levels in a bacteria culture to increase and nitrate levels to decrease when the bacteria culture comprises nitrate and a bacteria isolate or mixture consisting essentially of the nitrite-accumulating bacteria and where the composition is configured to release at least a portion of the bacteria in the oral cavity. In some embodiments, the probiotic composition comprises a bacteria isolate or mixture that comprises one or more of *Neisseria, Veillonella, Haemophilus, Actinomyces, Granulicatella, Prevotella, Leptotrichia, Brevibacillus, Porphyromonas, Fusobacterium*, and clade Gemellaceae, wherein the composition does not contain a contaminating amount of *Lactobacillus*.

Other aspects the disclosure relate to methods of making a probiotic composition and can comprise combining a bacteria isolate or mixture consisting essentially of nitrite-accumulating bacteria and a carrier to form a probiotic composition, where the nitrite-accumulating bacteria are bacteria that allow nitrite levels in a bacteria culture to increase and nitrate levels to decrease when the bacteria culture comprises nitrate and a bacteria isolate or mixture consisting essentially of the nitrite-accumulating bacteria. In some embodiments, the method further comprises making a dosage form of the probiotic composition, where the dosage form is a tablet, a capsule, a granule, powder, a gum, a biofilm, an oral liquid preparation, a food-product serving, or a lozenge. In some embodiments, the method further comprises combining nitrate, the bacteria isolate or mixture consisting essentially of nitrite-accumulating bacteria, and a carrier to form a probiotic composition.

Other aspects the disclosure relate to methods of making a probiotic composition and can comprise combining a bacteria isolate or mixture and a carrier to form a probiotic composition, where bacteria isolate or mixture comprises one or more of *Neisseria, Veillonella, Haemophilus, Actinomyces, Granulicatella, Prevotella, Leptotrichia, Brevibacillus, Porphyromonas, Fusobacterium*, and clade Gemellaceae and does not contain a contaminating amount of *Lactobacillus*. In some embodiments, the method further comprises making a dosage form of the probiotic composition, where the dosage form is a tablet, a capsule, a granule, powder, a gum, a biofilm, an oral liquid preparation, a food-product serving, or a lozenge. In some embodiments, the method further comprises combining nitrate, the bacteria isolate or mixture, and a carrier to form the probiotic composition.

Other aspects the disclosure relate to methods of screening a bacteria isolate or mixture for nitrite-accumulating capacity and can comprise anaerobically culturing a bacteria sample in a medium comprising a predetermined concentration of nitrate; detecting the levels of nitrate and the levels of nitrite in the medium after at least 10 hours, 11 hours, 12 hours, 13 hours, 14 hours, 16 hours, 18 hours, 24 hours, 30 hours, 36 hours, 42 hours, 48 hours, 60 hours, 72 hours or more of culturing (or any range derivable therein); and selecting the bacteria sample from a medium where the nitrate levels are decreased and the nitrite levels are increased to make a probiotic composition. In some embodiments, the method further comprises selecting the bacteria sample from a medium where the nitrate levels are decreased and the nitrite levels are increased two-fold, three-fold, four-fold, five-fold, or more after 48 hours of culturing. In some embodiments, the method further comprises selecting the bacteria sample from a medium where the nitrate levels are decreased by at least 50%, at least 60%, at least 70%, at least 80%, at least 90% or at least 95%, and the nitrite levels are increased after 48 hours of culturing. In some embodiments, the method further comprises selecting the bacteria sample from a medium where the nitrate levels are decreased by at least 50%, at least 60%, at least 70%, at least 80%, at least 90% or at least 95%, and the nitrite levels are increased two-fold, three-fold, four-fold, five-fold, or more after 24 hours, after 48 hours, after 72 hours, after 96 hours or more of culturing. The bacteria sample can consists essentially of bacteria that are naturally occurring in the oral cavity of a human.

Other aspects the disclosure relate to methods of measuring levels of nitric oxide and can comprise administering a probiotic composition to an oral cavity of a subject; measuring the levels of nitrite in the saliva or breath of the subject after 10 minutes to 3 hours of the administration; where the probiotic composition comprises a bacteria isolate or mixture comprising one or more of *Neisseria, Veillonella, Haemophilus, Actinomyces, Granulicatella, Prevotella, Leptotrichia, Brevibacillus, Porphyromonas, Fusobacterium*, and clade Gemellaceae and not containing a contaminating amount of *Lactobacillus*. In some embodiments, the method further comprises measuring the levels of nitrite in the saliva or breath of the subject before the administration. In some embodiments, the probiotic composition further comprises an effective amount of nitrate. In some embodiments, an increase in nitrite levels is observed. The increase in nitrite levels can be a 10%, 20%, 30%, 40%, 50%, 75%, 100%, 150%, 200%, or more from the nitrite level measured before the administration.

In particular embodiments, the probiotic compositions can comprise a bacteria isolate or mixture selected from a group consisting essentially of *Granulicatella, Neisseria, Prevotella, Haemophilus, Fusobacterium, Brevibacillus*, and clade Gemellaceae. For example, bacteria comprise one or more of the following: *Granulicatella adiacens, Haemophilus parainfluenzae, Actinomyces odontolyticus, Actinomyces viscosus, Actinomyces oris, Neisseria flavescens, Neisseria mucosa, Neisseria sicca, Neisseria subflava, Prevotella melaninogenica, Prevotella salivae, Veillonella dis-*

*par, Veillonella parvula, Veillonella atypical, Fusobacterium nucleatum,* and *Brevibacillus brevis.* In some embodiments, the bacteria of the probiotic composition consists essentially of nitrite-accumulating bacteria, where the nitrite-accumulating bacteria are bacteria that allow nitrite levels in a bacteria culture to increase and nitrate levels to decrease when the bacteria culture comprises bacteria isolate or mixture consisting essentially of the nitrite-accumulating bacteria. In some embodiments, the bacteria consists essentially of strains that contain nitrate-reductase encoding genes and do not contain nitrite-reductase encoding genes. In some embodiments, the bacteria consists essentially of strains that express one or more of the following nitrate reductase genes: narG, narL, narJ, narQ, narI, napC, napB, napH, napD, napA, napG, and napF. In some embodiments, the bacteria consists essentially of strains that do not express nitric oxide reductase. In some embodiments, the bacteria consists essentially of strains that do not express the following nitrite reductase genes: nirK, nirB, nirD, nrfF, nrfA, and nrfH. In some embodiments, the bacteria consists essentially of weak or non-acid producing bacterial strains. In some embodiments, the composition comprises 1 mg to 100 g of the bacteria. In some embodiments, the composition comprises an activity of 5 billion to 20 billion colony forming units. In some embodiments, the composition is in the form of a tablet, a granule, powder, a gum, a biofilm, an oral liquid preparation, a food product, or a lozenge. In some embodiments, the probiotic composition is stored at or below 45° C. In some embodiments, the bacteria are freeze-dried.

The probiotic compositions can be further defined by any combination of the following features. In some embodiments, the bacteria are genetically-modified or recombinant bacteria, where a gene encoding nitric oxide reductase is substantially suppressed. In some embodiments, the probiotic composition further comprises and effective amount of nitrate. In some embodiments, the probiotic composition further comprises a botanical source of nitrate. In some embodiments, the botanical source of nitrate comprises one or more of beet root, kale, artichoke, holy basil, gymnema sylvestre, ashwagandha root, salvia, St. John wort, broccoli, stevia, spinach, gingko, kelp, tribulus, eleuthero, epimedium, eucommia, hawthorn berry, rhodiola, green tea, codonopsys, panax ginseng, astragalus, pine bark, dodder seed, Schisandra, cordyceps, and mixtures thereof. In some embodiments, the probiotic composition further comprises one or more excipients, wherein the one or more excipients comprises a substance having a pH buffering capacity. In some embodiments, the pH buffering substance is selected form the group consisting of bicarbonates, carbamides, phosphates, proteins, salts, and combinations of two or more thereof. In some embodiments, the isolated bacteria are naturally present in oral microflora of a mammal and more particularly, a human. In some embodiments, the nitrite-accumulating bacteria are bacteria that allow nitrite levels in a bacteria culture to increase by at least two-fold when the bacteria culture comprises nitrate and a bacteria isolate or mixture consisting essentially of the nitrite-accumulating bacteria. In some embodiments, the nitrite accumulating bacteria are bacteria that reduce nitrate at a higher rate than reducing nitrite.

In addition, while method are presented as separate embodiments, it is to be understood that the steps recited therein can be combined in any combination to form another embodiment. For example, a method can comprise screening a bacteria isolate or mixture for nitrite-accumulating capacity and making a probiotic composition with the selected nitrite accumulating bacteria as a result of the screening. As such, a method can comprise 1, 2, 3, 4, 5, or more of the following steps (or any range derivable therein): culturing, such as anaerobically, a bacteria sample in a medium comprising a predetermined concentration of nitrate; detecting the levels of nitrate and the levels of nitrite in the medium after at least 10 hour of culturing; and selecting the bacteria sample from a medium where the nitrate levels are decreased and the nitrite levels are increased to make a probiotic composition; selecting the bacteria sample from a medium where the nitrate levels are decreased and the nitrite levels are increased two-fold after 48 hours of culturing; selecting the bacteria sample from a medium where the nitrate levels are decreased by at least 50% and the nitrite levels are increased after 48 hours of culturing; combining a bacteria isolate or mixture consisting essentially of nitrite-accumulating bacteria and a carrier to form a probiotic composition; making a dosage form of the probiotic composition; combining nitrate, the bacteria isolate or mixture consisting essentially of nitrite-accumulating bacteria, and a carrier to form a probiotic composition; combining a bacteria isolate or mixture and a carrier to form a probiotic composition; administering a probiotic composition, such as to an oral cavity, measuring the levels of nitrite in the saliva or breath of the subject after 10 minutes and up to 3 hours of the administration; and/or measuring the levels of nitrite in the saliva or breath of the subject before the administration. Other steps include culturing bacteria, expanding bacteria, which may or may not be isolated or purified, purifying bacteria, freezing bacteria, concentrating bacteria, enriching for bacteria, selecting particular bacteria, assaying bacteria, growing bacteria, and/or testing growth rate of the bacteria.

Any embodiment discussed with respect to one aspect can apply to other aspects of other embodiments disclosed herein as well.

The embodiments in the Example section are understood to be embodiments that are applicable to all aspects of the methods and compositions disclosed herein.

The term "effective," as that term is used in the specification and/or claims, means adequate to accomplish a desired, expected, or intended result. An "effective amount" is an amount adequate to effect desired, expected, or intended results. An effective amount can be administered in one or more administrations.

"Therapeutically effective amount" means that amount which, when administered to a subject for treating a condition, disease, or side effect, is sufficient to effect such treatment for the condition, disease, or side effect.

"Dosage form" refers to physically discrete units suitable as unitary dosages for human subjects and other mammals. Each dosage form can contain a predetermined quantity of the described bacteria and any other supplemental ingredients calculated to produce the desired onset, tolerability, and/or therapeutic effects.

"Oral administration" refers to a route of administration that can be achieved by contacting the dosage form with a surface of the oral cavity and can include swallowing, chewing, or sucking of an oral dosage form comprising the drug or nutritional formula.

"Treatment" or "treating" includes: (1) inhibiting a condition, disease, or side effect in a subject or patient experiencing or displaying the pathology or symptomatology of the condition, disease, or side effect (e.g., arresting further development of the pathology and/or symptomatology), (2) ameliorating a condition, disease, or side effect in a subject or patient that is experiencing or displaying the pathology or symptomatology of the condition, disease, or side effect (e.g., reversing the pathology and/or symptomatology), and/ or (3) effecting any measurable decrease in a condition, disease, or side effect in a subject or patient that is experiencing or displaying the pathology or symptomatology of the condition, disease, or side effect.

"Prevention" or "preventing" includes: (1) inhibiting the onset of a condition, disease, or side effect in a subject or patient who may be at risk and/or predisposed to the condition, disease, or side effect but does not yet experience or display any or all of the pathology or symptomatology of the condition, disease, or side effect, and/or (2) slowing the onset of the pathology or symptomatology of the condition, disease, or side effect in a subject or patient which may be at risk and/or predisposed to the condition, disease, or side effect but does not yet experience or display any or all of the pathology or symptomatology of the condition, disease, or side effect. As used herein, "attenuation" of a conditions or process includes results in which the condition or process is reversed or prevented.

As used herein, the term "patient" or "subject" refers to a living mammalian organism, such as a human, monkey, horse, cow, sheep, goat, dog, cat, mouse, rat, guinea pig, or transgenic species thereof. Non-limiting examples of human subjects are adults, juveniles, children, infants and fetuses.

"Pharmaceutically acceptable" means that which is useful in preparing a pharmaceutical composition that is generally safe, nontoxic and neither biologically nor otherwise undesirable and includes that which is acceptable for veterinary use as well as human pharmaceutical use.

It is contemplated that any embodiment discussed in this specification can be implemented with respect to any method or composition as disclosed herein, and vice versa. Furthermore, compositions as disclosed herein can be used to achieve the methods described herein.

It is also contemplated that any method described herein may be described using Swiss-type use language.

The use of the term "or" in the claims is used to mean "and/or" unless explicitly indicated to refer to alternatives only or the alternatives are mutually exclusive.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

Other objects, features and advantages of embodiments described herein will become apparent from the following detailed description. It should be understood, however, that the detailed description and the specific examples, while indicating specific embodiments, are given by way of illustration only, since various changes and modifications within the spirit and scope of the embodiments disclosed herein will become apparent to those skilled in the art from this detailed description.

BRIEF DESCRIPTION OF THE DRAWINGS

The following drawings form part of the present specification and are included to further demonstrate certain aspects as disclosed herein. Embodiments may be better understood by reference to one or more of these drawings in combination with the detailed description of specific embodiments presented herein.

DETAILED DESCRIPTION OF THE INVENTION

Figure 1:
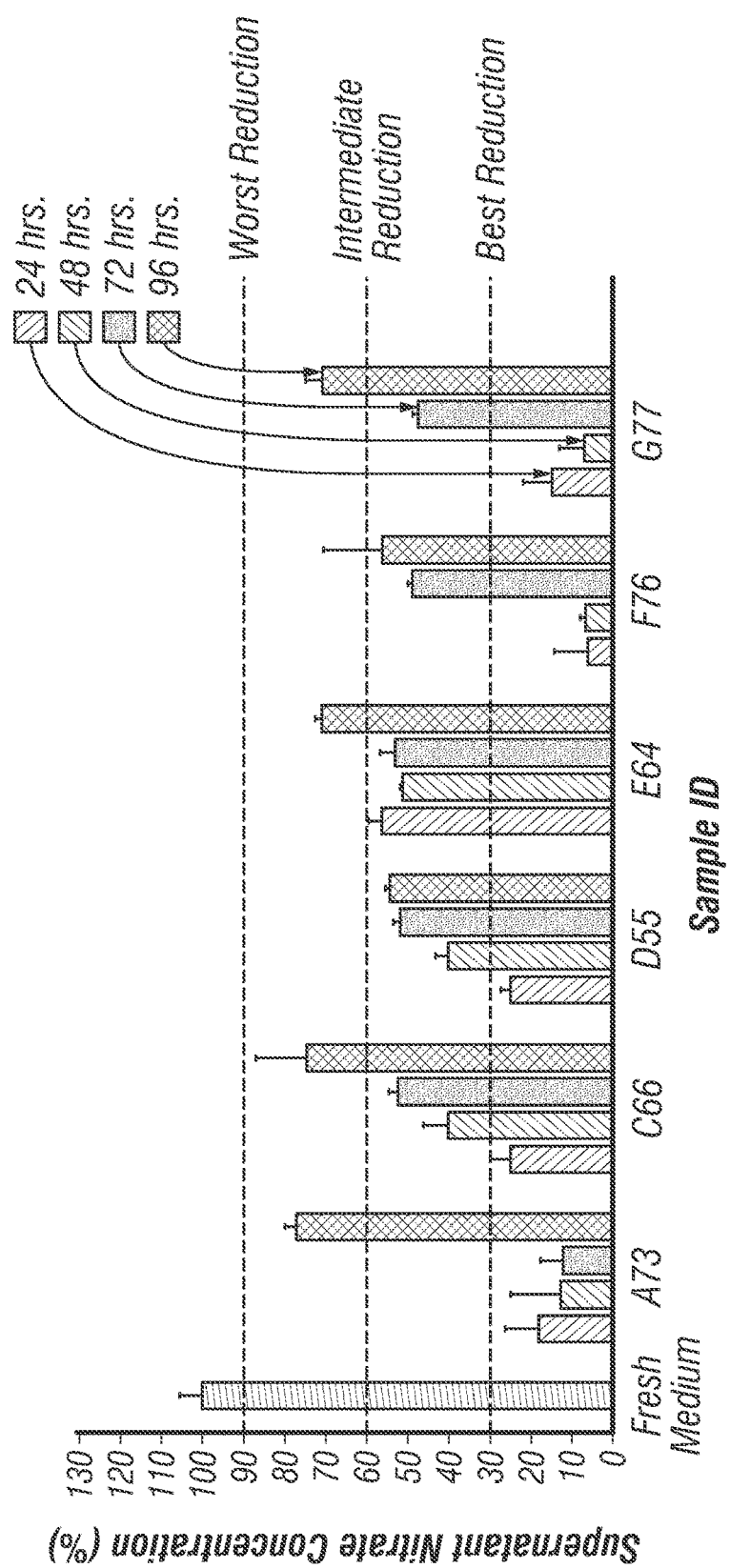
FIG. 1: The nitrate-reducing capacity of anaerobic biofilms inoculated with tongue-scrapings samples from six healthy volunteers. Each bar represents the percentage of nitrate remaining in the spent supernatant fluid after 24 hour increments of incubation. Samples were tested (and are presented for each sample from left to right on the bar graph as shown for sample G77) after 24 hours; 48 hours; 72 hours; and 96 hours. The data are the average±SEM of three individual experiments and are represented as a percent of the starting nitrate concentration in the medium. Dashed lines indicate cutoffs for placing samples in nitrate-reducing groups. Subject IDs (A73, C66, D55, E64, F76, G77) are indicated on the x-axis below each group of four bars.

The compositions and methods of the present disclosure promote nitric oxide (NO) production in vivo and treat/attenuate conditions of NO-insufficiency in a subject, particularly in the oral cavity of a subject, by fostering colonization of the oral cavity of the subject by specific oral bacteria or bacterial communities. The present invention is based, at least in part, on the finding that particular microorganisms are effective at reducing nitrate. In addition, the present invention is based, at least in part, on the finding that particular microorganisms are effective at reducing nitrate and ineffective at reducing nitrite. Such bacteria can be nitrite-accumulating bacteria because nitrite tends to accumulate as a result of their nitrate-reducing mechanisms. A composition of probiotics in accordance with the present disclosure reduces the amount of nitrate through nitrate reduction, while also allowing nitrite accumulation.

The present disclosure relates to probiotic compositions and methods of using the same. The probiotic compositions can comprise one or more isolated bacteria capable of enhancing nitrite or nitric oxide production. More particularly, the probiotic compositions comprise one or more isolated bacteria capable of reducing nitrate to nitrite. The probiotic compositions may further comprise one or more isolated bacteria not capable of reducing nitrite and/or producing nitric oxide. The probiotic compositions may also include one or more pharmaceutically acceptable carriers or excipients.

Bacteria strains capable of reducing nitrate and thereby promoting nitric oxide production can be used in the compositions and methods described herein. Bacteria isolate or mixture present in the compositions of the present disclosure expresses a gene that relates to nitrate reducing activity, such as a nitrate reductase gene. For example, the isolated bacteria can consists essentially of strains that express one or more of the following nitrate reductase genes: narG, narL, narJ, narQ, narI, napC, napB, napH, napD, napA, napG, and napF.

In some embodiments, a probiotic composition can comprise or consist essentially of a bacteria isolate or mixture that facilitate nitrite accumulation. In other words, the bacteria of the composition reduce nitrate at a higher rate than their ability to reduce nitrite, thereby yielding nitrite accumulation. For example, the bacteria isolate or mixture consists essentially of strains that do not express or only minimally express the following nitrite reductase genes: nirK, nirB, nirD, nrfF, nrfA, and nrfH.

Certain bacteria naturally present in the oral cavity have been discovered to facilitate nitrate reduction and even further, nitrite accumulation. In some embodiments, a probiotic composition can comprise or consist essentially of a bacteria isolate or mixture selected from the genera of *Granulicatella* (e.g., *G. adiacens*), *Haemophilus* (e.g., *H. parainfluenzae*), *Gemella* (e.g., *G. morbillorum*), *Brevibacillus* (e.g., *B. brevis*), *Veillonella* (e.g., *V. dispar, V. parvula,* and *V. atypical*), *Neisseria* (e.g., *N. mucosa, N. sicca, N. subflava,* and *N. flavescens*), *Actinomyces* (e.g., *A. odontlyticus, A. viscosus,* and *A. oris*), *Prevotella* (e.g., *P. salivae*), and *Fusobacterium* (e.g., *F. nucleatum*). In some embodiments, a composition can comprise a bacteria community consist essentially of one or more *Granulicatella, Neisseria, Prevotella, Haemophilus, Fusobacterium, Brevibacillus* and clade Gemellaceae (e.g., *Gemella* (*G.*) *haemolysins, G. morbillorum, G. bergeri, G. sanguinis, G. asaccharolytica; G. cuniculi,* and *G. palaticanis*). In some embodiments, the species of clade Gemellaceae in the composition consists essentially of clade Gemellaceae naturally present in the oral cavity of mammals and more particularly, humans. In some embodiments, the species of clade Gemellaceae in the composition consists essentially of *G. haemolysins* and/or *G. morbillorum*. In some embodiments, the species of clade Gemellaceae in the composition does not include *G. haemolysins, G. morbillorum, G. bergeri, G. sanguinis, G. asaccharolytica; G. cuniculi,* and *G. palaticanis*. Other bacteria suitable for use with the present disclosure may be determined using tests as described in the Examples to test and select for bacterial nitrate reduction and/or nitrite reduction capacities.

In some embodiments, the probiotic composition does not contain a detectable or contaminating amount of lactic acid bacteria, such as *Lactobacillus*. While note wishing to be bound by any particular theory, *Lactobacillus* may play an inhibitory role to nitrate reduction by producing some metabolic byproduct that shuts down or slows nitrate reduction in a bacteria community. The acid byproducts of *Lactobacillus* may be a factor in this regard. A contaminating amount of *Lactobacillus* would be an amount that would inhibit nitrate reduction or prevent nitrite accumulation in a culture from other bacteria in the community. It was observed in the examples that a *Lactobacillus* amount of 0.008% in a community was not contaminating, that an amount 7.5% was mildly contaminating, and that 22% was lead to the worst nitrate reduction. Therefore, in some embodiments, a non-contaminating amount would be equal to or less than 5%, 4%, 3%, 2%, 1%, 0.5%, or 0.1% of lactic acid bacteria, such as *Lactobacillus*, in the probiotic composition. Other lactic acid bacteria genera include *Leuconostoc, Pediococcus, Lactococcus, Streptococcus, Aerococcus, Carnobacterium, Enterococcus, Oenococcus, Sporolactobacillus, Tetragenococcus, Vagococcus,* and *Weisella*. Other undesired bacteria genera can include *Bifidobacterium, Acetobacter* and *Acetobacterium*. In some embodiments, probiotic composition does not contain a contaminating amount of acid-tolerant bacteria.

In addition to the above-mentioned bacteria, the probiotic compositions of the present disclosure can comprise supplemental ingredients. Supplemental ingredients can be metabolic precursors for the bacteria community. In some embodiments, the supplemental ingredient can be an energy substrate, vitamin, or mineral utilized by the bacteria. In some embodiments, such ingredients are a nitrate source, such as an inorganic nitrate source or salt (e.g., calcium nitrate, sodium nitrate, potassium nitrate, and/or magnesium nitrate) or an botanical nitrate source (e.g., beet root, kale, artichoke, holy basil, gymnema sylvestre, ashwagandha root, salvia, St. John wort, broccoli, stevia, spinach, gingko, kelp, tribulus, eleuthero, epimedium, eucommia, hawthorn berry, rhodiola, green tea, codonopsys, panax ginseng, astragalus, pine bark, dodder seed, Schisandra, cordyceps, and mixtures thereof.) The addition of nitrate permits the bacteria in the composition to efficiently generate nitrite. In some embodiments, the composition can comprise an amount at or between 5 mg to 20 g of a botanical nitrate source, such as a dehydrated botanical source of the plants listed above. In some embodiments, the composition can comprise 5 mg to 1000 mg or 10 mg to 500 mg of a nitrate salt, or any amount or range therebetween.

Other supplemental ingredients can include nitrite salts (sodium nitrite, potassium nitrite, calcium nitrite and/or magnesium nitrite. Some embodiments can comprise 1 mg to 100 mg of nitrite salts. Addition of nitrite may prevent pathogenic bacteria in the oral cavity from proliferating and disrupting the oral nitrate reducing bacterial communities. Addition of nitrite may allow for the colonization and proliferation of nitrate reducing bacteria, particularly in the early dosing phase.

Therapeutic Applications:

The compositions of the present disclosure can be administered to a subject to promote a healthy oral or gut microflora. The diversity of oral and gut microflora can become diminished or altered through the use of antibiotics, mouthwash, and other bactericides. Some diversity, particularly of the nitrate-reducing and/or nitrite-accumulating bacteria, can be selectively reestablished to promote oral health and cardiovascular health.

Administration of the oral formulation can lessen the impact of aging on cytoprotective mechanisms. In an aspect of the present disclosure, use of an oral formulation in a subject can oppose, attenuate, or reverse NO-deficiency-related effects on these mechanisms. In a particular example, attenuation of NO deficiency can be achieved by increasing NO production processes and pathways in a subject, as well as by up-regulating NO processes and pathways. As used herein, "subject" refers to a mammal that may benefit from the administration of a composition or method as recited herein. Most often, the subject will be a human. In a particular aspect the oral formulation is effective in opposing, attenuating, or reversing NO-deficiency-related disorders.

Continuous generation of NO is essential for the integrity of the cardiovascular system and a decreased production and/or bioavailability of NO is central to the development of cardiovascular disorder. Previous studies have demonstrated that nitrite therapy given intravenously prior to reperfusion protects against hepatic and myocardial VR injury. Oral nitrite has also been shown to reverse L-NAME induced hypertension and serve as an alternate source of NO in vivo. Additionally, experiments in primates revealed a beneficial effect of long-term application of nitrite on cerebral vasospasm. Moreover, inhalation of nitrite selectively dilates the pulmonary circulation under hypoxic conditions in vivo in sheep. Topical application of nitrite improves skin infections and ulcerations. Furthermore, in the stomach, nitrite-derived NO seems to play an important role in host defense and in regulation of gastric mucosal integrity. Studies demonstrate that plasma nitrite levels progressively decrease with increasing cardiovascular risk. Since a substantial portion of steady state nitrite concentrations in blood and tissue are derived from dietary sources, modulation of nitrite and/or nitrate intake can provide a first line of defense for conditions associated with NO insufficiency. In fact, it has been reported that dietary nitrate reduces blood pressure in healthy volunteers.

The composition of the present disclosure can be administered to a subject to enhance nitric oxide levels in the oral cavity or the blood stream. Through the enhancement of nitric oxide levels, cardiovascular disease can be attenuated. In one embodiment, the present invention can provide a novel therapy for patients experiencing myocardial infarction, stroke, or injury from ischemia-reperfusion insult. Several embodiments provide patients with an extended-release formulation via the administration of compositions containing nitrate-reducing probiotics and may further contain nitrate, among additional components. Such compositions can be administered upon onset of symptoms to provide at least some protection from injury until the patient can be provided with reperfusion therapy, such as in a hospital setting.

In several embodiments, the present invention relates to the administration of nitrate-reducing probiotics that may be combined with nitrate as a preventive agent in cardiovascular disease or as treatment to inhibit the progression of and reverse atherosclerosis or reduce hypertension. In some embodiments, nitrate acts as an extended release nitrite source that is absorbed and re-circulated through the enterosalivary pathway and is reduced to nitrite by the nitrate-reducing bacteria present in the composition. Therefore, several embodiments effectively provide an extended availability of nitrite, which is beneficial to optimal cardiovascular health. Stated differently, the nitrate-reducing probiotics present the compositions described herein provide a continuous mode of reducing nitrate to nitrite and supplied nitrate can serve as a reservoir to be converted into nitrite to increase the reservoir of nitric oxide.

Certain embodiments of the present invention disclosed herein provide a formulation and a process to enhance and extend the therapeutic half-life of nitrite and therefore increase nitric oxide (NO) bioavailability. Thus, several embodiments provide the basis for new preventive or therapeutic strategies in diseases associated with NO insufficiency and new guidelines for optimal health as well as extend the therapeutic window in which one may intervene during a heart attack. Extension of nitrite half-life is desirable in the design of cardioprotective therapeutics or preventative medicines. As such, several embodiments prevent the onset or progression of cardiovascular or heart disease and protect from myocardial infarction thru nitrate-reducing probiotic supplementation. Furthermore, certain embodiments provide an extended half-life of nitrite, out to 1 hour, which is the "golden hour" in terms of recovery from heart attack and stroke.

Dosage and Formulation:

The probiotic compositions described herein are preferably formulated for oral administration to a subject. Dosage forms include a tablet, a granule, powder, a gum, a biofilm, an oral liquid preparation, a food product, or a lozenge, as well as other traditional dosage forms for oral administration (such as mouth washes, toothpastes, and the like). The compositions of the present invention have particular utility in the area of human and veterinary therapeutics. Generally, administered dosages will be effective to deliver femtomolar to micromolar concentrations of the isolated bacteria to the appropriate site, such as the oral cavity or another section of the gastrointestinal tract whether upper or lower. The amount of the described bacteria isolate or mixture that is administered or prescribed to the subject can be about, at least about, or at most about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 g, or any range derivable therein. In some embodiments, the probiotic composition comprises 0.1 g to 10 g or 1 g to 5 g of bacteria isolate or mixture. In some embodiments, the composition can comprise a bacteria isolate or mixture as described with an activity of 0.5 to 100 billion colony forming units or 5 billion to 20 billion colony forming units or 8 billion to 12 billion colony forming units. When provided in a discrete amount, each intake of described bacteria or composition comprising the bacteria can be considered a "dose" and present in a dosage form. A medical practitioner may prescribe or administer multiple doses over a particular time course (treatment regimen) or indefinitely. Examples of well-known oral dosage forms include tablets, capsules, caplets, powders, granulates, beverages, syrups, gels, elixirs, mouth sprays or washes, confections, or other food items, melt tablets, hard-boiled candies, chewy candies, gummies, oral films, and liquid as well as powder formulations for intraoral and pulmonary inhalation.

Dosage forms can be formulated to affect the viability of the probiotics upon administration, as well as the rate, extent, and duration of probiotic activity. Dosage forms such as chewing gums, candies, quick-dissolving lozenge or strip, or powders, in particular, reconstitutable powders offer advantages over the traditional dosage forms for oral administration. For example, each of these dosage forms avoids hepatic first pass metabolism, degradation within the gastrointestinal tract, and probiotic and other active ingredient loss during absorption. Consequently, the amount of the active bacteria and supplemental ingredients (such as nitrate) required per dose can be less than that which would be required if formulated, for example, in a pill or tablet for oral administration. Similarly, with each of these dosage forms, the bioavailability of the bacteria and supplemental ingredients is increased, thereby reducing the time to onset of therapeutic activity, such as nitric oxide production. Thus, in some embodiments, the oral formulations described herein are formulated to be "controlled release" formulations. "Controlled release", as used herein, signifies a release of an active agent or ingredient from an oral formulation in the oral cavity of the subject, whereby active sucking, chewing, or other manipulation of the oral formulation is controlling the amount of active agent released. For example, gum, lozenges, and hard candies can facilitate a controlled-release.

In some embodiments, the dosage forms can be formulated to combine with a liquid carrier moments prior to administration, such as a reconstitutable powder. The liquid carrier can be water, and can be recommended to be at room temperature or slightly warm. The reconstitutable powder composition can further comprise an energy substrate to facilitate activation of the bacteria.

In some embodiments, the composition further comprises a carrier. As used herein, the term "carrier" refers to a typically inert substance used as a diluent or vehicle for a drug such as a therapeutic agent. The term also encompasses a typically inert substance that imparts cohesive qualities to the composition and can also enhance the viability or activity of the probiotics, particularly if freeze dried. Suitable carriers can be lyoprotectants and matrix forming additives that protect the bacteria during the freeze-drying process. Examples of lyoprotectants and matrix forming additives comprise albumin, mannitol, sucrose, betaine, gum acacia, and trehalose. Other suitable carriers for use in the compositions described herein include, without limitation, a solid, semi-solid, or liquid such as a binder or a gum base. Non-limiting examples of binders include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, VEEGUM®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. These binders can be pre-processed to improve their flowability and taste by methods known in the art such as freeze drying [see, e.g., "Fundamentals of Freeze-Drying," Pharm. Biotechnol., Vol. 14, pp. 281-360 (2002); "Lyophililization of Unit Dose Pharmaceutical Dosage Forms," Drug. Dev. Ind. Pharm., Vol. 29, pp. 595-602 (2003)]; solid-solution preparation; and lubricant dusting and wet-granulation preparation with a suitable lubricating agent (see, e.g., Remington: The Science and Practice of Pharmacy, supra). For example, MANNOGEM® and SORBOGEM®, sold by SPI Pharma Group (New Castle, Del.), are freeze-dried, processed forms of mannitol and sorbitol, respectively. Typically, when a binder is included in the formulation, the compositions of the present invention comprise from about 15% to about 90% by weight of the binder, and preferably from about 35% to about 80%. However, one skilled in the art will appreciate that the compositions of the present invention can be made without any binders, e.g., to produce a highly friable dosage form.

In some embodiments, the carrier can comprise a gum base. Non-limiting examples of gum bases include materials selected from among the many water-insoluble and saliva-insoluble gum base materials known in the art. For example, in some instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000). Typically, the gum base comprises from about 25% to about 75% by weight of these polymers, and preferably from about 30% to about 60%.

Other suitable carriers can additionally include lubricating agents; wetting agents; emulsifying agents; solubilizing agents; suspending agents; preserving agents such as methyl-, ethyl-, and propyl-hydroxy-benzoates, butylated hydroxytoluene, and butylated hydroxyanisole; sweetening agents; flavoring agents; coloring agents; and disintegrating agents (i.e., dissolving agents) such as crospovidone as well as croscarmellose sodium and other cross-linked cellulose polymers. Lubricating agents can be used to prevent adhesion of the dosage form to the surface of the dies and punches, and to reduce inter-particle friction. Lubricating agents may also facilitate ejection of the dosage form from the die cavity and improve the rate of granulation flow during processing. Examples of suitable lubricating agents include, without limitation, magnesium stearate, calcium stearate, zinc stearate, stearic acid, simethicone, silicon dioxide, talc, hydrogenated vegetable oil, polyethylene glycol, mineral oil, and combinations thereof. The compositions of the present invention can comprise from about 0% to about 10% by weight of the lubricating agent, and preferably from about 1% to about 5%.

In some embodiments, the carrier can comprise one or more sweetening agents. Sweetening agents can be used to improve the palatability of the composition by masking any unpleasant tastes it may have. Examples of suitable sweetening agents include, without limitation, compounds selected from the saccharide family such as the mono-, di-, tri-, poly-, and oligosaccharides; sugars such as sucrose, glucose (corn syrup), dextrose, invert sugar, fructose, maltodextrin, and polydextrose; saccharin and salts thereof such as sodium and calcium salts; cyclamic acid and salts thereof; dipeptide sweeteners; chlorinated sugar derivatives such as sucralose and dihydrochalcone; sugar alcohols such as sorbitol, sorbitol syrup, mannitol, xylitol, hexa-resorcinol, and the like, and combinations thereof. Other suitable sweeting agents may include natural plant-based sweeteners such as stevia. Hydrogenated starch hydrolysate, and the potassium, calcium, and sodium salts of 3,6-dihydro-6-methyl-1 1,2,3-oxathiazin-4-one-2,2-dioxide may also be used. Of the foregoing, sorbitol, mannitol, and xylitol, either alone or in combination, are preferred sweetening agents. The compositions of the present disclosure can comprise from about 0% to about 80% by weight of the sweetening agent, from about 5% to about 75%, or from about 25% to about 50%.

In some embodiments, the carrier can comprise one or more flavoring agents. Flavoring agents can also be used to improve the palatability of the composition. Examples of suitable flavoring agents include, without limitation, natural and/or synthetic (i.e., artificial) compounds such as peppermint, spearmint, wintergreen, cinnamon, menthol, cherry, strawberry, watermelon, grape, banana, peach, pineapple, apricot, pear, raspberry, lemon, grapefruit, orange, plum, apple, fruit punch, passion fruit, chocolate (e.g. white, milk, dark), vanilla, caramel, coffee, hazelnut, combinations thereof, and the like.

In some embodiments, the carrier can comprise one or more coloring agents. Coloring agents can be used to color code the composition, for example, to indicate the type and dosage of the bacteria therein. Suitable coloring agents include, without limitation, natural and/or artificial compounds such as FD & C coloring agents, natural juice concentrates, pigments such as titanium oxide, silicon dioxide, and zinc oxide, combinations thereof, and the like. The compositions of the present disclosure can comprise from about 0% to about 10% by weight of the flavoring and/or coloring agent, preferably from about 0.1% to about 5%, and more preferably from about 2% to about 3%.

The dosage form to be administered will, in any event, contain a quantity of the bacteria in a therapeutically effective amount for developing a particular microflora (at least temporarily) within a region of the gastrointestinal tract, such as the oral cavity. In addition, the dosage form can contain a therapeutically effective amount of supplemental ingredients to promote the therapeutic function of the bacteria, e.g., reducing nitrate to nitrite.

Methods for preparing such dosage forms are known or will be apparent to those skilled in the art. For example, in some embodiments, a chewing gum dosage form can be prepared according to procedures standard in the industry. In other embodiments, a tablet, lozenge, or candy dosage form (e.g., a sucker) can be prepared according to the procedures set forth in, for example, Remington's "The Science and Practice of Pharmacy, 20th Ed.," Lippincott, Williams & Wilkins (2003); and, "Pharmaceutical Dosage Forms, Volume 1: Tablets," 2nd Ed., Marcel Dekker, Inc., New York, N.Y. (1989). The probiotic ingredients can be combined with any other supplemental ingredients or carriers according to procedures standard in formulating probiotic compositions.

Freeze-drying:

Some embodiment of the present disclosure comprise freeze-dried bacteria. The described bacteria can be cultured in liquid medium, and then collected by centrifugation to remove the liquid medium. Alternatively, cells can be harvested from agar plates.

The collected bacteria can then be suspended in volume of lyophilization medium (e.g., in equal volumes) that comprises a lyoprotectant(s) and a matrix agent(s) that allow the sample to retain its shape during and after processing. Disaccharides such as sucrose and trehalose can be used as lyoprotectants. Matrix forming additives, often referred to as excipients, include mannitol, BSA, serum, and skim milk. This bacteria/lyophilization medium mixture can be partitioned into aliquots and transferred into a sterile vessel to undergo the lyophilization process.

Techniques of lyophilization are known or will be apparent to those skilled in the art. Examples are described in Guergoletto et al. (2012). "Dried Probiotics for Use in Functional Food Applications—Methods and Equipment," ISBN: 978-953-307-905-9, InTech, Available from: http://www.intechopen.com/books/food-industrialprocesses-methods-and-equipment/dried-probiotics-for-use-in-functional-food-applications and Gitaitis, "Refinement of Lyophilization Methodology for Storage of Large Numbers of Bacterial Strains" *Plant Disease,* 71: 615-616 (1987), which are hereby incorporated by reference.

The freeze-dried bacteria can be combined with any carrier and any secondary

Administration:

Administration of the compositions of the present invention may preferably carried out via any of the accepted modes of administration to the mucous membranes of the oral cavity. Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. These regions differ from each other with respect to their anatomy, drug permeability, and physiological response to drugs. Preferably, the compositions of the present invention are administered to the sublingual mucosa, buccal mucosa, or a combination thereof.

The oral mucosa, possessing a rich blood supply and suitable drug permeability, is an especially attractive route of administration for systemic delivery of therapeutic agents. Furthermore, delivery of a therapeutic agent across the oral mucosa bypasses hepatic first pass metabolism, avoids enzymatic degradation within the gastrointestinal tract, and provides a more suitable enzymatic flora for drug absorption. As used herein, the term "sublingual delivery" refers to the administration of a therapeutic agent across the mucous membranes lining the floor of the mouth and/or the ventral tongue. The term "buccal delivery" as used herein refers to the administration of a therapeutic agent across the mucous membranes lining the cheeks.

The sublingual mucosa is the most highly permeable region of the oral cavity, and provides rapid absorption and high bioavailability of a drug in a convenient, accessible, and well-accepted route of administration [Harris, et al., supra]. Suitable sublingual dosage forms include, without limitation, tablets (e.g., quick-dissolving, slow-dissolving), lozenges, candy, and soft gelatin capsules filled with liquid drug. Such systems create a very high drug concentration in the sublingual region before they are systemically absorbed across the sublingual mucosa. As a result, the sublingual mucosa is particularly well-suited for producing a rapid onset of action, and sublingual dosage forms can be used to deliver drugs with shorter delivery period requirements and/or less frequent dosing regimens. Although the buccal mucosa is considerably less permeable than the sublingual area, rapid absorption and high bioavailability of a drug can also be observed with buccal administration. Suitable buccal dosage forms include, without limitation, chewing gums, tablets (e.g., quick-dissolving, slow-dissolving), lozenges, candy, and the like. Both the buccal mucosa and the sublingual mucosa are far superior to the gastrointestinal tract for providing increased absorption and bioavailability of a drug.

To increase the permeability of drugs through the oral mucosa, the composition can further comprise penetration enhancers. The penetration enhancers may be of the type that alters the nature of the oral mucosa to enhance penetration, or of the type that alters the nature of the therapeutic agent to enhance penetration through the oral mucosa. Suitable penetration enhancers include, without limitation, polyoxyethylene 23-lauryl ether, aprotin, azone, benzalkonium chloride, cetylpyridinium chloride, cetyltrimethylammonium bromide, cyclodextrin, dextran sulfate, lauric acid, propylene glycol, lysophosphatidylcholine, menthol, methoxysalicylate, methyloleate, oleic acid; phosphatidylcholine, polyoxyethylene, polysorbate 80, sodium ethylenediaminetetraacetic acid ("EDTA"), sodium deoxycholate, sodium glycocholate, sodium glycodeoxycholate, sodium lauryl suflate, sodium salicylate, sodium taurocholate, sodium taurodeoxycholate, as well as certain sulfoxides and glycosides, and combinations thereof.

It should be noted that while delivery through the oral mucosa is a preferred route, any method of delivery that delivers the bacteria and any supplemental ingredients to a suitable section of the gastrointestinal tract can be utilized. In particular, any method that would deliver the bacteria as well as any supplemental ingredients to the mucosal wall where they can begin to act therapeutically can be utilized. Such alternative mucosal delivery formulations including but not limited to suppositories (both rectal and vaginal), sprays (both oral and nasal), subdermal implants, and controlled release capsules that allow the formulation to move past the stomach region of the patient, e.g., pH controlled release capsules.

The probiotic composition may be administered 1, 2, 3, 4, 5, 6, 7, 8, 9, 10, 11, 12, 13, 14, 15, 16, 17, 18, 19, 20, 30, 40, 50, 60, 70, 80, Or more times or any range derivable therein. It is further contemplated that the dose may be taken for an indefinite period of time or for as long as the subject exhibits symptoms of the medical condition for which the described isolated bacteria was prescribed or to prevent or inhibit such conditions. Also, the dose may be administered every 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more, or any range derivable therein. Alternatively, it may be administered systemically over any such period of time and be extended beyond more than a year.

In some embodiments, the dose regiment comprises at least two parts. A first dose comprises the nitrate-reducing bacteria as described herein. The second dose comprises nitrate that can be released into the oral cavity at time subsequent to the initial bacteria dose to provide a later supply of nitrate.

Nitrite Level Testing:

Some embodiments of the present disclosure relate to measuring the nitrite levels before and/or after probiotic compositions of the present disclosure have been administered. For example, a method of measuring levels of nitric oxide can comprise administering a probiotic composition to a subject as described herein and measuring the levels of nitrite in the saliva or breath of the subject after 10 minutes to 4 hours or 1 hour to 3 hours or 30 minutes to 2 hours of the administration and/or prior to administration. The test methods and compositions for measuring nitrite levels are described in U.S. Patent Publication No. 2012/0321724, which is hereby incorporated by reference in its entirety. Testing methods and reagents can utilize a Griess reagent to detect the presence of nitrite.

Genetically Modified Strains:

In some embodiments, the bacteria suitable for use in accordance with the present disclosure may be genetically modified. The genetically modified bacterial strains may include bacteria that are modified to have nitrate reducing activity or an enhancement of such activity. In further embodiments, the genetically modified bacterial strains may include bacteria that are genetically modified bacterial strains to have nitrite reducing activity or an enhancement of such activity. Some embodiments can comprise bacterial strains modified to have nitric oxide producing activity or an enhancement of such activity. It will be appreciated that the term "genetically modified", as used herein indicates any modification of DNA sequences coding for genes involved in the expression of NO activities including modifications of sequences that regulate the expression of genes coding for such enzymatic activities. Accordingly, genetic modification can be based on construction or selection of mutants of one or more selected bacteria, or it can be based on recombinant DNA-technology. As used herein, the term "mutant" is used in the conventional meaning of that term; i.e., it refers to strains obtained by subjecting a lactic acid bacterial strain to any conventionally-used mutagenization treatment including treatment with a chemical mutagen such as ethanemethane sulphonate (EMS) or N-methyl-N'-nitro-N-nitroguanidine (NTG), UV light or to spontaneously occurring mutants which are selected on the basis of a modified NO activity. Although it is presently preferred to provide the genetically modified bacteria according to the invention by random mutagenesis or by selection of spontaneously occurring mutants, i.e., without the use of recombinant DNA technology, mutants of a selected bacteria can be provided by such technology including site-directed mutagenesis and PCR techniques and other in vitro or in vivo modifications of DNA sequences coding for NO activities or sequences regulating the expression of genes coding for the NO activities. Genetically modified bacteria can also be formed by conventional recombinant DNA-technology including insertion of sequences coding for NO activities, e.g. by replacing a native promoter for such coding sequences by a foreign promoter which either enhances or reduces the expression of the coding sequences. Moreover, selected bacterial strains can be derived from species that do not have an inherent capability to reduce nitrate, reduce nitrite, or otherwise produce NO or NO precursors by inserting genes coding for such activities isolated from a different organism comprising such genes. The source of such genes may be bacterial species, yeast species or mammal species. Additionally, genetically modified bacteria can be constructed by modifying metabolic pathways in a bacterium that are not directly involved in nitric oxide (NO) pathways. It will be appreciated that the expression "under cofactor conditions" as used herein indicates the absence/presence in an appropriate medium of any non-protein substance required for biological activity of any of the enzyme activities according to the invention, including but not limited to $NAD^+$, NADH, $NADP^+$ and NADPH. siRNA can also be used to silence a gene where expression is not desired, such as a nitrite reductase gene.

In some embodiments, genetically-modified or recombinant bacteria can have been modified to suppress or eliminate one or more of the following nitrite reductase genes: nirK, nirB, nirD, nrfF, nrfA, and nrfH. In some embodiments, genetically-modified or recombinant bacteria can have been modified to express one or more of the following nitrate reductase genes: narG, narL, narJ, narQ, narI, napC, napB, napH, napD, napA, napG, and napF.

In some embodiments, a method of screening or selectively enhancing a bacteria isolate or mixture for nitrite-accumulating capacity can comprise anaerobically culturing a bacteria sample in a medium comprising a predetermined concentration of nitrate; detecting the levels of nitrate and the levels of nitrite in the medium after at least 10 hour of culturing; and selecting the bacteria sample from a medium where the nitrate levels are decreased and the nitrite levels are increased to make a probiotic composition. Screening a bacteria can comprise selecting the bacteria sample from a medium where the nitrate levels are decreased and the nitrite levels are increased two-fold after 72 hours, 48 hours, 24 hours, 12 hours, or 6 hours of culturing, or any value therebetween. Screening selecting the bacteria sample from a medium where the nitrate levels are decreased by at least 50% and the nitrite levels are increased after 72 hours, 48 hours, 24 hours, 12 hours, or 6 hours of culturing, or any value therebetween.

EXAMPLES

The following examples are included to demonstrate preferred embodiments of the inventions. It should be appreciated by those of skill in the art that the techniques disclosed in the examples which follow represent techniques discovered by the inventor to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the inventions.

Materials and Methods:

Subject population and microbiological sampling: All human subjects research was reviewed and approved by the Committee for the Protection of Human Subjects were recruited from the faculty, staff, and students of the University of Texas Health Science Center at Houston. Six subjects were evaluated for oral health, including the use of a standard periodontal exam, with spot probing for bleeding and loss of attachment, and an oral health subject history. Six subjects were selected according to the following inclusion and exclusion criteria. Inclusion criteria: over the age of 18 and capable of giving consent, bleeding on probing at less than 10% of sites, greater than 24 teeth, no attachment loss of more than 4 mm, no clinical history of bone loss, no oral hard or soft tissue lesions, no use of antibiotics within the previous 3 months. Exclusion criteria: bleeding on probing at more than 10% of sites, less than 24 teeth, attachment loss of more than 4 mm at any site, clinical history of bone loss, presence of oral hard or soft tissue lesions, recent use of antibiotics within the previous 3 months. Samples were collected using a sterile stainless steel tongue scraper, passed once over the tongue dorsum from back to front with gentle pressure. Tongue-scraping samples were transferred into 1 ml of reduced transport medium (0.045% $K_2HPO_4$, 0.045% $KH_2PO_4$, 0.09% NaCl, 0.09% $(NH_4)_2SO_4$, 0.018% $MgSO_4$, 0.038% EDTA, 0.04% $Na_2CO_3$, 0.02% dithiothreitol, 0.2% Bacto-agar, 5% glycerol) in Nunc freezer vials with a sterile swab, and placed on wet ice for immediate transport to storage at −80° C. Prior to freezing, a portion of each tongue-scraping sample was dispensed into 50 µl aliquots for use as inoculum for the in vitro biofilm assays. An additional 50 µl aliquot was dispensed into a collection tube from the MoBio PowerSoil Kit (MoBio, Carlsbad, Calif.), and frozen for transport to the Human Genome Sequencing Center (HGSC) at Baylor College of Medicine (BCM) for DNA extraction and 16S rRNA gene pyrosequencing. All samples were de-identified and assigned random numbers (A73, C66, D55, E64, F76, and G77).

In vitro biofilm assays: Aliquots of tongue-scraping samples (50 µl per well) were used as the inoculum for the generation of in vitro biofilm communities on sterile coated poly-methyl-methacrylate (PMMA) disks (0.4 cm) in 24-well sterile polystyrene tissue culture plates (Falcon). The PMMA disks in each well were coated with 600 µl of 20% fetal bovine serum (FBS) in carbonate buffer (pH 9.5) and incubated overnight at 4° C. The next day the FBS solution was removed and replaced with 500 µl of Biofilm Medium (BioM), composed of 45% trypticase soy broth (TSB) (Difco) supplemented with 7.6 µM hemin (Sigma) and 2.9 µM menadione (Sigma), 15% FBS, 10% phosphate buffered saline (PBS), and 12.8 mM $Na_2CO_3$. Each well was inoculated with the tongue-scrapping sample and the plate was then incubated at 37° C. in an anaerobic chamber (Coy) for 24 hr, under an atmosphere of 86% $N_2$, 10% $CO_2$, and 4% $H_2$. For nitrate-reduction assays, every 24 hr the spent medium was removed and replaced with 500 µl of fresh BioM. The recovered spent medium was centrifuged and 325 µl of the supernatant (spent medium) was transferred to a 0.5 µl tube and stored at 4° C. for subsequent assessment of the nitrate and nitrite content. Spent medium was collected at 24, 48, 72, and 96 hr, and the assays were repeated independently three times. For the microbiome analysis of each sample, one PMMA disk was removed at 24, 48, 72, and 96 hr, placed directly into a MoBio PowerSoil Kit sample tube, and frozen on dry ice for transport to the CMMR at BCM.

Assessment of nitrate and/or nitrite concentration: Each spent medium sample was added to an equal volume of ice-cold methanol, immediately vortexed and centrifuged at 13,200 rpm for 10 min to precipitate the protein and any remaining cells. Combined nitrate and nitrite (NOx) analysis was performed with a dedicated ENO-20 HPLC System (EiCom Corporation, San Diego, Calif.) (Bryan and Grisham 2007). This system is sensitive and selective for the measurement of NOx in all biological matrices. To separate nitrite and nitrate, the nitrate was first reduced to nitrite through a reaction with cadmium and reduced copper inside a reduction column. The two resolved peaks were then mixed with Griess reagent (dinitrogen trioxide, $N_2O_3$, generated from acidified nitrite that reacts with sulfanilamide) in-line to form the classical diazo compound, which was then detected spectrophotometrically. Triplicate determinations were performed on each specimen and the final values were averaged.

Microbial DNA Extraction, 16S rRNA Gene Amplification and Pyrosequencing: Bacterial genomic DNA was extracted from the initial tongue-scraping samples and the PMMA disks. DNA was extracted using the MoBio PowerSoil Kit following protocols benchmarked as part of the NIH Human Microbiome Project. The V3-V5 regions of the 16S rRNA gene were amplified using 454-pyrosequencing. Sequencing was performed at the HGSC at BCM using a multiplexed 454-Titanium sequencer.

16S data analysis: Sequence processing and analysis was performed using QIIME version 1.6.0 (Caporaso, Kuczynski et al. 2010). The sequencing file was de-multiplexed and quality filtered according to the following parameters: permitted sequence length between 200 bp and 1000 bp, a required minimum average quality score of 35 over a 50 bp sliding window, no homopolymer longer than 6 bp, no ambiguous bases allowed, two primer mismatches allowed, and one barcode mismatch allowed. Quality trimming of 16S rRNA gene sequences resulted in 190,722 high quality sequences with an average of 6357 sequences per sample. Sequences were clustered de novo and binned into OTUs based on 97% identity (equivalent of species), assigned taxonomy using RDP Classifier trained to the GreenGenes database (October 2012 release), and singleton reads were removed from the dataset. Before alpha diversity metrics were calculated, the OTU table was subsampled to 4910 reads per sample 5 times; the average values across the 5 subsampled OTU tables were used to calculate alpha diversity metrics. Prior to beta diversity analysis, the OTU table was subsampled to 5008 reads, the smallest number of reads associated with any one sample. Unweighted UniFrac analysis was then performed to assess community similarity between samples; PCoA and Bi Plots were created from the UniFrac distance matrix to visualize sample clustering and taxa associated with clusters. ANOSIM was used to determined cluster tightness. Pie charts were used to visualize the mean relative abundances of genera present in each group of samples. Supervised machine learning using the random Forest algorithm identified specific OTUs that discriminated between groups.

Whole genome shotgun sequencing and analysis: Based on the results of the 16S rRNA gene pyrosequencing and analysis, three representative samples were chosen, one from each nitrate-reduction group, and performed whole genome shotgun (WGS) sequencing. Bacterial genomic DNA isolated from sample F76-2 (best reduction), F76-3 (intermediate reduction), and A73-4 (worst reduction) was sequenced on one lane of the Illumina HiSeq (2×150) platform at the HGSC at BCM. An average of 156.7 million reads was obtained per sample, with an average of 84.6% Q30 bases. FASTQ sequencing files were quality trimmed (leading N's removed, sequence truncated at the first N thereafter) and aligned against the human genome (hg19) and PhiX to filter out known contaminants. Using a custom perl script, the trimmed, filtered FASTQ files were interleaved into one FASTQ file, which was converted to FASTA format. To obtain taxonomic classification of the bacterial taxa present in each sample, the WGS FASTA file for each sample passed through MetaPhlAn (Segata, Waldron et al. 2012), a computational tool that relies on clade specific marker genes for taxonomic assignment of unassembled WGS data. Further, to assess gene content in these three samples, the sequence data passed through USEARCH (32-bit version), using the KEGG v54 prokaryotic database as the reference databases, and further passed the resulting files through HUMAnN (Abubucker, Segata et al. 2012), a computational tool that takes BLAST/Usearch outputs and provides information about pathway coverage and abundance.

Bacterial strain isolation, identification, and culture conditions: The strains assessed for nitrate reduction are low passage human isolates from the oral bacteria collection of GDT. The strains selected for use were originally isolated from two volunteer donors. For general strain isolation, plaque or saliva samples were serially diluted in TSB and aliquots were plated on non-selective blood agar plates. The bacterial plates were incubated at 37° C. under anaerobic conditions for 48 hours to seven days. From each bacterial plate, well-isolated colonies were identified using a dissecting microscope, recovered with a sterile inoculating needle, and repeatedly sub-cultured on blood agar plates to obtain pure cultures. For each purified strain, DNA was extracted, PCR-amplified with universal 16s rDNA primers (27F, 1492R ((Stackebrandt, Witt et al. 1991)), and the resulting PCR product submitted for Sanger sequencing encompassing the V3-V5 hyper variable region (SeqWright). Sequence data was subsequently assembled, trimmed to remove low quality data, and compared to the Human Oral Microbiome Database (Dewhirst, Chen et al. 2010) 16S rDNA RefSeq by local BLAST (CLC Genomics Workbench). Isolates were assigned to a matching genus at 95-97% identity, and a matching genus and species at >97% identity. *Veillonella dispar* UTDB 1-3 and *Fusobacterium nucleatum* spp *polymorphum* UTDB 1-5 were originally isolated from dental plaque from the same subject, and strains *Actinomyces odontolyticus* UTDB 59-1 and *Streptococcus mutans* UTDB 59-3 were isolated from saliva from a second subject. For this study, all four strains were grown anaerobically at 37° C. in a Coy anaerobic chamber under an atmosphere of 86% $N_2$, 10% $CO_2$, 2% $NaHCO_3$, 7.5 µM hemin and 3 µM menadione. TSB blood agar plates (BAP) were made with the addition of 5% sheep's blood and 1.5% agarose. The medium for *V. dispar* was supplemented with 2% lactate prior to cultivation.

Identification of nitrate and nitrite reductase genes in the genome sequences of candidate species: the following commercially available candidate species were obtained: *Prevotella melaninogenica* strain D18 (ATCC 25845, GenBank Accession Number ACWY00000000.1), *Neisseria mucosa* strain C102 (ATCC 25996, GenBank Accession Number ACDX00000000.2), *Fusobacterium nucleatum* subsp. *polymorphum* strain F0401 (BEI HM-260D, NCBI Reference Sequence NZ_ADDB00000000.2), *Granulicatella adiacens* type strain GaD (ATCC 49175, GenBank Accession Number ACKZ00000000.1) and *Haemophilus* oral taxon 851 strain F0397 (*Haemophilus parainfluenzae*, BEI HM-469, GenBank Accession Number AGRK00000000.1). The whole genome sequences for these strains were obtained, and BLASTX was used to determine which of these strains encoded nitrate and/or nitrite reductase genes. A BLASTX reference database was created from the available sequences for the following nitrate and nitrite reductase genes: nirK, nirB, nirD, narG, narL, narJ, narQ, narI, nrfF, nrfA, nrfH, napC, napB, napH, napD, napA, napG, and napF. *Haemophilus* oral taxon 851 encodes both nitrate and nitrite reductase genes, while *Granulicatella adiacens*, *Prevotella melaninogenica* and *Fusobacterium nucleatum* subsp. *polymorphum* encode only nitrite reductase genes. Results were inconclusive for *Neisseria mucosa*, although it appears that it likely encodes both nitrate and nitrite reductase genes.

The isolate species described above were not sequenced, and thus their genome sequences could not be searched in silico for the presence of nitrate and nitrite reductase genes. Instead, the genome sequences of all sequenced strains available on NCBI were collected and BLASTX was used, as described above, to determine which of the nitrate and nitrite reductase genes listed above were encoded by which strains. The strains used were: *Actinomyces odontolyticus* ATCC 17982 (GenBank Accession number AAYI00000000.2), *Veillonella dispar* ATCC 17748 (GenBank Accession Number ACIK00000000.2), *Fusobacterium nucleatum* subsp. *polymorphum* F0401 (NCBI Reference Sequence NZ_ADDB00000000.2), and *Fusobacterium nucleatum* subsp. *polymorphum* ATCC 10953 (NCBI Reference Sequence NZ_AARG00000000.1). As described above, *Fusobacterium nucleatum* subsp. *polymorphum* F0401 encodes only nitrate reductase genes, and *Fusobacterium nucleatum* subsp. *polymorphum* ATCC 10953 also encodes only nitrite reductase genes. Conversely, *Actinomyces odontolyticus* ATCC 17982 encodes only nitrate reductase genes, and *Veillonella dispar* ATCC 17748 encodes both nitrate and nitrite reductase genes.

Results:

Diversity of the human tongue microbiome from initial scrapings and biofilms grown for four days: Tongue-scraping samples from six healthy volunteers were obtained from the dorsal surface of the tongue, as it has been previously shown that most nitrate reduction occurs at this location in the oral cavity (Doel, Benjamin et al. 2005). As revealed by 16S rRNA gene pyrosequencing and analysis, the tongue scrapings were diverse, with an average of 230.1 operational taxonomic units (OTUs) detected in these samples. The majority of OTUs in the original samples belonged to *Streptococcus* (20.2%+/−9.75%), *Veillonella* (14.1%+/−4.15%), *Prevotella* (11.8%+/−5.88%), *Neisseria* (10.8%+/−9.62%), and *Haemophilus* (8.64%+/−4.93%), although there was notable variation observed among the samples (see Table 1). These results mirror those of the HMP Consortium's human microbiome project, which also found that *Veillonella*, *Prevotella*, *Haemophilus*, and *Streptococcus* were found in abundance on the tongue dorsum of healthy individuals (Consortium 2012).

TABLE 1

The top ten genera present in individual tongue scrapings are shown.

| Genus | Abundance | Genus | Abundance | Genus | Abundance |
|---|---|---|---|---|---|
| Sample A73 | | Sample C66 | | Sample D55 | |
| Haemophilus | 18.0% | Prevotella | 21.5% | Streptococcus | 35.7% |
| Streptococcus | 15.4% | Streptococcus | 13.1% | Veillonella | 19.5% |
| Neisseria | 15.1% | Neisseria | 10.1% | Prevotella | 10.4% |
| Veillonella | 14.0% | Veillonella | 8.55% | Haemophilus | 4.55% |
| Prevotella | 8.65% | Haemophilus | 7.89% | Actinomyces | 3.25% |
| Porphyromonas | 5.19% | Porphyromonas | 6.67% | Leptotrichia | 2.84% |
| Granulicatella | 3.04% | Unclassified Genera | 5.13% | Unclassified Genera | 2.10% |
| Unclassified Genera | 2.38% | [Prevotella] | 2.99% | Granulicatella | 1.76% |
| Unclassified Genera | 1.94% | Leptotrichia | 2.82% | Oribacterium | 1.46% |
| Actinomyces | 1.16% | Megasphaera | 2.21% | Fusobacterium | 1.38% |
| Sample E64 | | Sample F76 | | Sample G77 | |
| Streptococcus | 28.0% | Neisseria | 26.9% | Streptococcus | 18.7% |
| Porphyromonas | 18.2% | Veillonella | 11.8% | Veillonella | 18.3% |
| Veillonella | 12.2% | Streptococcus | 10.2% | Prevotella | 15.7% |
| Haemophilus | 6.34% | Haemophilus | 9.59% | Neisseria | 9.82% |
| Prevotella | 5.03% | Prevotella | 9.49% | Haemophilus | 5.47% |
| Unclassified Genera | 4.33% | Porphyromonas | 6.62% | Fusobacterium | 3.50% |
| Neisseria | 2.69% | Capnocytophaga | 3.38% | Porphyromonas | 3.22% |
| Fusobacterium | 2.57% | Leptotrichia | 3.28% | Actinomyces | 2.13% |
| [Prevotella] | 1.73% | Fusobacterium | 2.10% | Granulicatella | 1.96% |
| Capnocytophaga | 1.45% | Actinomyces | 1.95% | Leptotrichia | 1.69% |

After the first 24 hours of biofilm incubation, an average of 82.2 OTUs were detected, equating to an average loss of 147.9 OTUs when compared to the tongue scrapings (Table 2). As the biofilms incubated over a total period of four days, a continual decrease in richness was observed, until by day four the biofilms consisted of an average of only 24.6 OTUs (Table 2). Notably, the biofilms were dominated by *Streptococcus*, in contrast with what was observed in the tongue scrapings, which are expected to represent the steady-state population in the native environment. These results suggest that streptococci are most adept at growing in this biofilm environment; however, all five of the genera that were most abundant in the original inocula (*Streptococcus, Veillonella, Prevotella, Neisseria*, and *Haemophilus*) were also detected in the biofilms. These data reveal that communities of bacteria change in culture (some grow and others do not) and allow us to monitor these changes and correlate changes in communities with changes in nitrate reduction in order to identify which bacteria in complex communities are primarily responsible for nitrate reduction.

TABLE 2

The number of OTUs associated with each sample at a sequencing depth of 4,910 reads is listed. The OTU table was randomly subsampled to 4,910 reads per sample five times; OTU values listed are an average of the five subsamplings. Averages per time point are also listed.

| | Tongue scraping | 24 hour biofilm | 48 hour biofilm | 72 hour biofilm | 96 hour biofilm |
|---|---|---|---|---|---|
| Subject A73 | 197.6 | 68.4 | 53.6 | 20.8 | 19.4 |
| Subject C66 | 278 | 128.8 | 88.4 | 58 | 37.6 |
| Subject D55 | 211.2 | 72 | 35.4 | 33.4 | 16 |
| Subject E64 | 199 | 62.6 | 52.6 | 33.2 | 24.6 |
| Subject F76 | 247.2 | 92.6 | 132.4 | 69.6 | 32.8 |
| Subject G77 | 247.8 | 71.6 | 55.4 | 31.6 | 17 |
| Average | 230.1 | 82.2 | 69.6 | 41.1 | 24.6 |

Nitrate reduction by bacterial biofilms differs between samples and decreases over time: The activity of a bacterial biofilm community can be defined based on its consumption of nutrients. Of interest was nitrate metabolism. Biofilm nitrate reduction was defined by the amount of nitrate remaining in the biofilm medium after 24 hours of growth. The nitrate content of the biofilm growth medium was approximately 30 µM prior to inoculation. Every 24 hours, corresponding with PMMA disc collection, the spent medium was carefully removed and replaced with fresh medium, and the amount of nitrate remaining in the spent medium was determined. It is noted that nitrate reduction was not assessed for the initial inoculum (tongue scraping). However, the 24-hour time point is unique in that bacteria in the well include all of the bacteria from the original inoculum—those that attach to the substrate and those that do not. Thus, the nitrate consumption in the medium of the 24-hour samples represents the nitrate-reducing capacity of the entire population of the original tongue scraping—those bacteria that formed biofilms and those that did not but could still contribute to nitrate reduction at some point over the first 24 hour period. All subsequent samples (48, 72, and 96 hours) reflect the nitrate-reducing capacity of those cells either in the biofilm or previously associated with the biofilm.

There was a wide range in nitrate-reducing capacity over 96 hours across the six samples, and the longer the samples incubated, the lower the nitrate-reduction activity became, until by 96 hours only 20-45% of the activity remained (see FIG. 1). These changes in nitrate reductase concomitant with changes in bacterial communities in culture allowed for investigation into the loss of activity with the loss of specific bacteria. The samples could be separated into 4 groups based on their capacity for nitrate reduction. The first group, consisting only of sample A73, maintained a high level of nitrate reduction for the first three days. The second group, consisting of samples F76 and G77, was similar to group 1 in that these samples maintained a high level of nitrate-reducing activity for days 1 and 2, but they began to lose their activity by day 3. The third group, containing samples C66 and D55, did not efficiently reduce, even during the first 24 hours, and the little activity they had was quickly lost. The last group, containing only sample E64, never efficiently reduced nitrate. The biofilm samples were regrouped based on their apparent nitrate-reducing activity, regardless of sample of origin or incubation time. The first group was designated "best reducers" and contained nine samples (A73-1, A73-2, A73-3, C66-1, D55-1, F76-1, F76-2, G77 1, and G77-2) that reduced at least 70% of the medium nitrate, the second group was designated "intermediate reducers" and contained ten samples (C66-2, C66-3, D55-2, D55-3, D55-4, E64-1, E64-2, E64-3, F76-3, and G77-3) that reduced between 40% and 70% of the medium nitrate, and the third group was designated "worst reducers" and contained five samples (A73-4, C66-4, E64-4, F76-4, and G77-4) that reduced less than 40% of the medium nitrate. The reduced nitrate thresholds for each group are illustrated in FIG. 1.

Specific genera appear to be associated with nitrate-reduction capacity: To define the specific taxonomic changes in the biofilms, the samples were first compared through Unweighted UniFrac-based principal coordinates analysis (PCoA). The six tongue scraping samples clustered together, indicating the initial composition of the microbial communities, were similar across all subjects. However, once the tongue-scraping samples were inoculated into the biofilm environment, the community composition became more variable as the samples "fanned out" across PC1 and down PC2 without forming tight clusters based on reduction capacity (ANOSIM R statistic=0.4701, p=0.01). A general trend was noted in that as nitrate reduction decreased, samples moved from left to right across PC1 and up PC2. Such a gradient is not surprising, as some amount of nitrate reduction occurs in both the intermediate and worst reducing samples and thus it is likely that some of the taxa responsible for nitrate reduction in the best nitrate reducing samples are also present to some extent in the intermediate and worst nitrate reducing samples. To visualize which taxa were driving differences between samples on the PCoA plot, a Bi Plot was generated. It was observed that *Neisseria, Veillonella, Haemophilus, Porphyromonas, Fusobacterium, Prevotella*, and *Leptotrichia* were more prevalent in an area of the PCoA plot near a cluster of best nitrate-reducing samples, *Brevibacillus, Granulicatella*, and oral bacteria of Gemellaceae were more prevalent near a cluster consisting of best and intermediate reducing samples, and *Lactobacillus* was more prevalent in an area of the PCoA plot near worst-reducers. The presence of *Neisseria, Veillonella, Haemophilus, Porphyromonas, Fusobacterium, Prevotella, Leptotrichia, Brevibacillus*, and *Granulicatella* near the best nitrate reducing samples suggested that members of these genera may significantly contribute to nitrate reduction in the oral cavity.

Figure 2A:
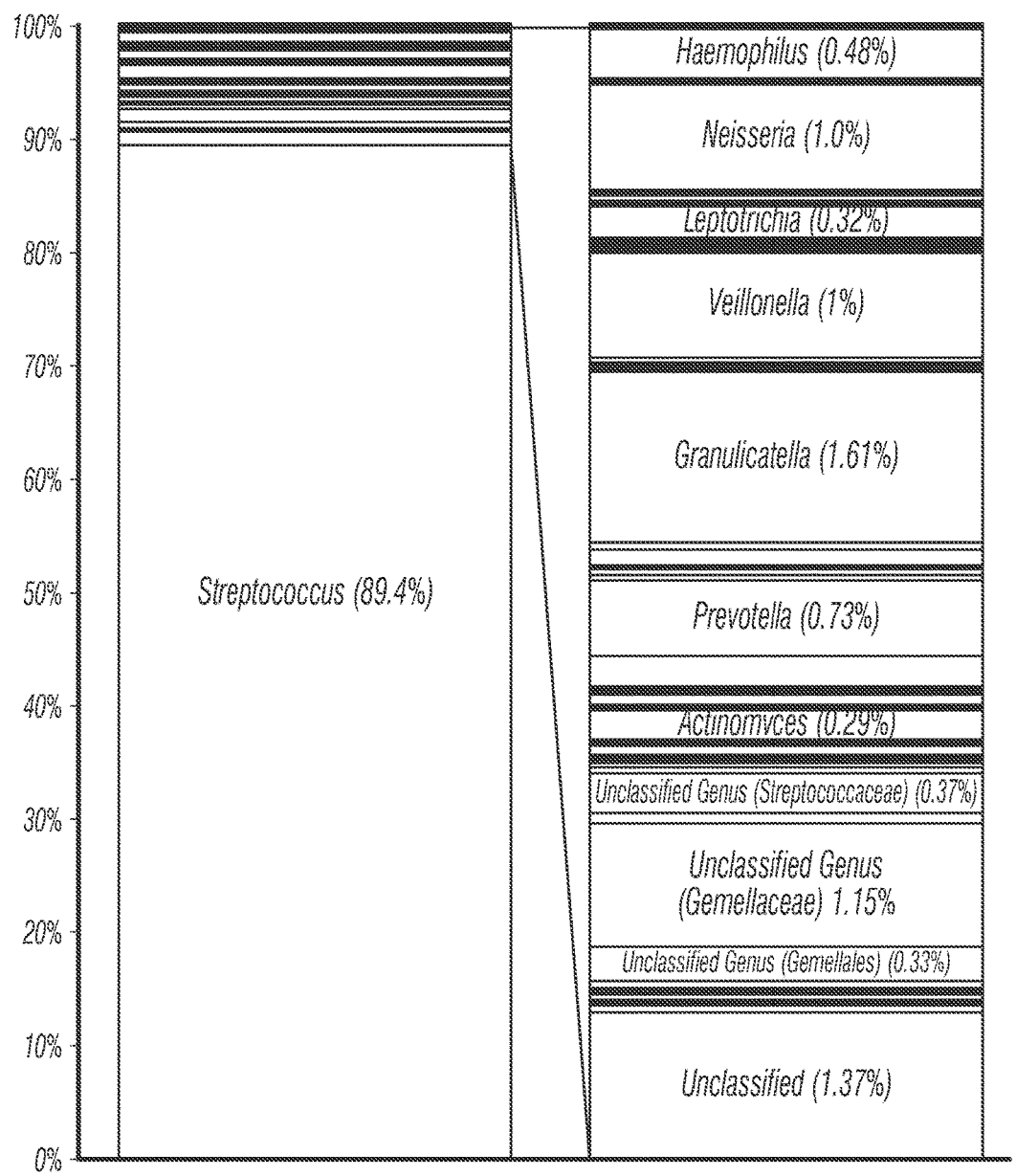
FIG. 2: The mean relative abundance of genera present in each group of nitrate reducers. Bar charts with insets depict the mean relative abundance of genera present A) in the best (n=9), B) intermediate (n=10), and C) worst (n=5) nitrate-reduction groups. Inset bars depict all genera detected in each group except *Streptococcus*, which was the most abundant genus detected in all groups and is depicted in the main bars. The percent abundance and taxonomic classification of the most abundance taxa are noted on the graphs.
Figure 2B:
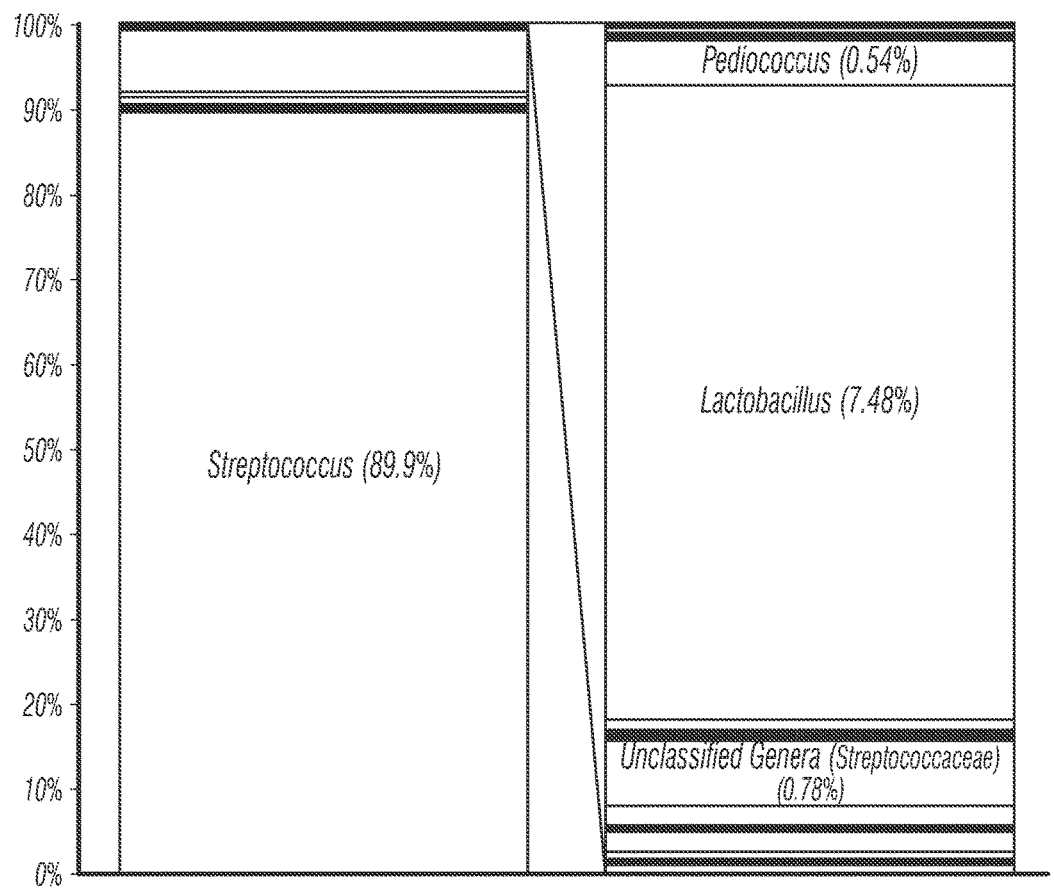
Figure 2C:
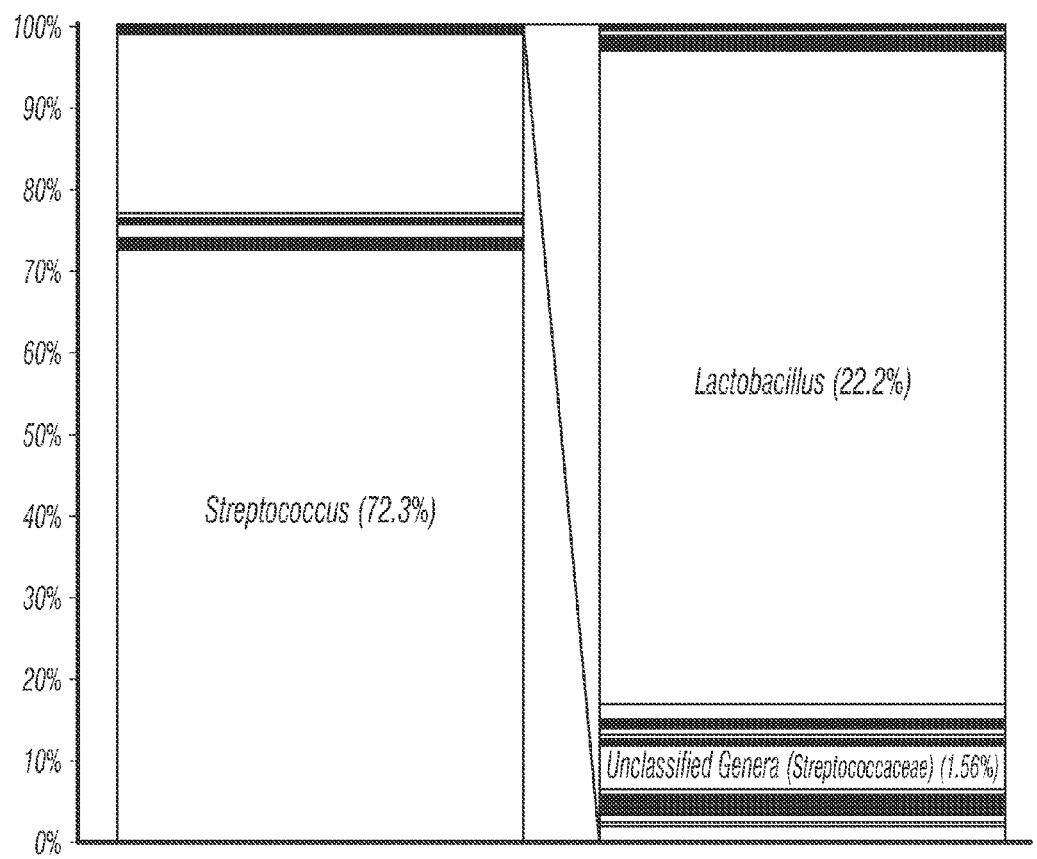

The mean relative abundances of taxa classified to the genus level present in each nitrate-reducing group (FIGS. 2A to 2C showing the mean relative abundance of the best, intermediate, and worst nitrate reducers, respectively) was determined. The streptococci were the most abundant taxa present in all three groups, and the mean relative abundance of this taxon did not notably change across the three groups. However, a number of taxa decreased as nitrate reduction decreased. The most notable decreases were observed in *Granulicatella* (1.61% relative abundance in the best nitrate-reducing group vs. 0.62% relative abundance in the worst nitrate-reducing group), *Veillonella* (1.0% vs. 0.15%), *Neisseria* (1.0% vs. 0.22%), *Actinomyces* (0.29% vs. 0.007%), *Prevotella* (0.73% vs. 0.26%), *Haemophilus* (0.48% vs. 0.08%), *Fusobacterium* (0.13% vs. 0.0075%), and Unclassified genera of the Gemellaceae family (1.15% vs. 0.64%). All of these taxa, with the exception of *Granulicatella*, clustered closely with best nitrate-reducing samples on the Bi Plot (*Granulicatella* was closer to a mixed cluster of best and intermediate reduction samples).

Interestingly, although *Lactobacillus* was almost undetected in the best nitrate-reducing group (0.008%), it comprised 7.48% of the biofilm community in the intermediate nitrate-reducing group and was the second most abundant genus (22.2%) in the worst nitrate-reduction group. Notably, half of the intermediate reducing samples originated from subjects C66 and D55, which never reduced nitrate well over four days of biofilm incubation, contained large proportions of *Lactobacillus*. Thus, while not wishing to be bound by any particular theory, *Lactobacillus* may play an inhibitory role by producing some metabolic byproduct that shuts down nitrate reduction in the community. The acid byproduct of *Lactobacillus* may be a factor in this regard.

Supervised machine learning was used to identify OTUs that discriminate between the groups with the best and worst nitrate reduction, and thus may potentially be utilized in future diagnostics. Ten OTUs classified to the family or genus level were identified that discriminated between the best and worst nitrate-reducing groups (see Table 3 below). Importantly, 8 of the 9 best nitrate-reducing samples were classified correctly by randomForest as best nitrate-reducing samples, corresponding to an estimated classification error rate of 11.1%, and all five of the worst nitrate-reduction samples were classified correctly, corresponding to an estimated error rate of 0%. Therefore, it appears that the randomForest-identified discriminatory OTUs are truly discriminatory and not spurious identifications. Correlating with the results discussed above, the ten discriminatory OTUs belonged to the Streptococcaceae and Gemellaceae families and the *Streptococcus, Haemophilus, Brevibacillus, Granulicatella*, and *Actinomyces* genera.

TABLE 3

OTUs identified through supervised machine learning (randomForest) to discriminate between best and worst nitrate reducing groups. The OTU ID#, taxonomic classification, and mean decrease in sample classification accuracy upon removal of the OTU from the dataset are listed.

| OTU ID# | Taxonomy | Mean Decrease in Accuracy |
| --- | --- | --- |
| 440 | Streptococcaceae | 1.49% |
| 759 | *Streptococcus [infantis]* | 1.19% |
| 897 | Gemellaceae | 1.05% |
| 894 | *Haemophilus [parainfluenzae]* | 1.04% |
| 589 | *Streptococcus* | 0.970% |
| 281 | Streptococcaceae | 0.888% |
| 8 | *Brevibacillus* | 0.837% |
| 1040 | *Granulicatella* | 0.809% |
| 976 | Gemellaceae | 0.804% |
| 244 | *Actinomyces* | 0.775% |

Identification of species present in a subset of samples through whole genome shotgun (WGS) sequencing: To identify the species belonging to the candidate genera identified through 16S rRNA gene pyrosequencing, WGS sequencing was performed on a subset of samples. The DNA from one sample from each nitrate-reduction group (best, intermediate, and worst) was sequenced and the data were analyzed using MetaPhlAn, a computational tool that assigns taxonomy down to the species level and determines percent abundance based on clade-specific marker genes (Segata, Waldron et al. 2012). Comparing the 16S and WGS data for these three samples, it was noted that at the phylum level, nearly the same results were obtained, detecting slightly more Proteobacteria and Actinobacteria with WGS sequencing (data not shown), and not unexpectedly, more unclassified taxa through 16S sequencing. At the genus level, the same top seven genera was detected in the 16S and WGS best and intermediate nitrate-reducing samples, albeit at slightly different relative abundances between sequencing method; conversely, most of the top ten genera detected via 16S sequencing in the worst nitrate-reducing sample were unclassified, whereas all of the top ten genera detected in this sample through WGS sequencing were assigned taxonomic classification. These small differences are likely due to the greater depth of sequencing provided by WGS sequencing, which surveys all genes rather than focusing on just one gene and facilitates more accurate taxonomic assignment.

Fourteen species were present at an abundance of at least 0.1% in the best nitrate-reducing sample and at the highest abundance in this sample compared to the intermediate and worst reducing sample, and belonged to the genera of interest identified through 16S rRNA gene pyrosequencing and analysis: *Granulicatella adiacens, Haemophilus parainfluenzae, Actinomyces odontolyticus, Actinomyces viscosus, Actinomyces oris, Neisseria flavescens, Neisseria mucosa, Neisseria sicca, Neisseria subflava, Prevotella melaninogenica, Prevotella salivae, Veillonella dispar, Veillonella parvula,* and *Veillonella atypica*. Additionally, *Fusobacterium nucleatum* and *Brevibacillus brevis* were designated as species of interest even though they were not at a relative abundance of at least 0.1% in the WGS best nitrate-reducing sample. Table 4 lists these 14 candidate species, along with the abundances of each of these species in the best, intermediate, and worst nitrate-reducing samples.

TABLE 4

The 14 candidate species detected through WGS sequencing and analysis of one representative sample from each group are listed. The percent abundance of the species in the all three nitrate-reducing groups is listed.

| Species | Best nitrate reducer % abundance | Intermediate nitrate reducer % abundance | Worst nitrate reducer % abundance |
| --- | --- | --- | --- |
| Neisseria flavescens | 3.65 | 1.40 | 0.004 |
| Haemophilus parainfluenzae | 3.12 | 0.93 | 0.017 |

TABLE 4-continued

The 14 candidate species detected through WGS sequencing and analysis of one representative sample from each group are listed. The percent abundance of the species in the all three nitrate-reducing groups is listed.

| Species | Best nitrate reducer % abundance | Intermediate nitrate reducer % abundance | Worst nitrate reducer % abundance |
| --- | --- | --- | --- |
| Neisseria mucosa | 2.53 | 0.792 | 0.001 |
| Prevotella melaninogenica | 2.22 | 1.35 | 0.020 |
| Granulicatella adiacens | 1.56 | 1.16 | 0.941 |
| Veillonella dispar | 1.34 | 0.587 | 0.002 |
| Veillonella atypica | 0.816 | 0.301 | 0.002 |
| Veillonella parvula | 0.566 | 0.256 | 0.009 |
| Neisseria sicca | 0.369 | 0.146 | 0.0004 |
| Prevotella salivae | 0.189 | 0.071 | 0 |
| Actinomyces odontolyticus | 0.162 | 0.068 | 0.006 |
| Actinomyces viscosus | 0.124 | 0.064 | 0.002 |
| Actinomyces oris | 0.124 | 0.072 | 0.0003 |
| Neisseria subflava | 0.119 | 0.043 | 0 |

Metabolic pathway reconstruction reveals a general uniformity in the abundances of metabolic pathways present in samples analyzed through WGS: To determine which metabolic pathways were present in the three samples analyzed through WGS, and whether any pathways were either present or absent in one sample compared to the other two, the WGS data was analyzed using MetaPhlAn, an analysis tool that provides information regarding metabolic pathway coverage and abundance based on the gene content of the dataset. The three samples were very similar in terms of both pathway coverage and abundance, with only minor differences observed. The same top eight pathways shown in Table 5 below were found across all samples, and the abundances of these pathways were comparable. Importantly, the abundance of the nitrogen-metabolism pathway, while slightly lower in the worst nitrate-reduction sample (coverage was also slightly lower in this sample), did not differ drastically between the three groups (see Table 5). This is in contrast to the in vitro data for these three samples, which showed that these samples differed notably in their ability to reduce nitrate.

TABLE 5

Coverage and abundance determined via HUMAnN, for the top eight most abundant pathways in the three samples that underwent WGS sequencing and analysis are shown. Also shown is the nitrogen metabolism pathway, which was not one of the most abundant pathways in the samples listed. The pathway coverage (presence/absence) measure is the relative confidence of each pathway being present in the sample and is expressed as a fraction between 0 and 1. The pathway abundance measure is the relative copy number of each pathway and is calculated from the gene abundance information (relative gene abundances are calculated from USEARCH results in which each read has been mapped to zero or more gene identifiers based on the quality of the match. The total weight of each read is 1.0, distributed over all gene (KO) matches by quality).

| | Best Nitrate Reducer | | Intermediate Nitrate Reducer | | Worst Nitrate Reducer | |
| --- | --- | --- | --- | --- | --- | --- |
| Pathway | Coverage | Abundance | Coverage | Abundance | Coverage | Abundance |
| ko00471: D-Glutamine and D-glutamate metabolism | 0.833333 | 0.0321196 | 1 | 0.0323382 | 1 | 0.0323028 |
| ko00290: Valine, leucine and isoleucine biosynthesis | 0.818182 | 0.0317484 | 0.818182 | 0.032204 | 0.772727 | 0.0333221 |
| ko00550: Peptidoglycan biosynthesis | 0.72973 | 0.0267444 | 0.702703 | 0.0293467 | 0.72973 | 0.0318703 |
| ko00970: Aminoacyl-tRNA biosynthesis | 0.46875 | 0.0267403 | 0.46875 | 0.026297 | 0.453125 | 0.0262222 |
| ko03010: Ribosome | 0.381944 | 0.0267307 | 0.381944 | 0.0246808 | 0.375 | 0.0253348 |
| ko00473: D-Alanine metabolism | 1 | 0.0252826 | 1 | 0.0268489 | 0.8 | 0.0282271 |

TABLE 5-continued

Coverage and abundance determined via HUMAnN, for the top eight most abundant pathways in the three samples that underwent WGS sequencing and analysis are shown. Also shown is the nitrogen metabolism pathway, which was not one of the most abundant pathways in the samples listed. The pathway coverage (presence/absence) measure is the relative confidence of each pathway being present in the sample and is expressed as a fraction between 0 and 1. The pathway abundance measure is the relative copy number of each pathway and is calculated from the gene abundance information (relative gene abundances are calculated from USEARCH results in which each read has been mapped to zero or more gene identifiers based on the quality of the match. The total weight of each read is 1.0, distributed over all gene (KO) matches by quality).

| Pathway | Best Nitrate Reducer | | Intermediate Nitrate Reducer | | Worst Nitrate Reducer | |
|---|---|---|---|---|---|---|
| | Coverage | Abundance | Coverage | Abundance | Coverage | Abundance |
| ko00061: Fatty acid biosynthesis | 0.538462 | 0.0236807 | 0.576923 | 0.0240604 | 0.538462 | 0.0260604 |
| ko00660: C5-Branched dibasic acid metabolism | 0.583333 | 0.0227483 | 0.583333 | 0.02317 | 0.583333 | 0.0236178 |
| ko00910: Nitrogen metabolism | 0.424242 | 0.00664097 | 0.393939 | 0.0058295 | 0.30303 | 0.00523466 |

Figure 3:
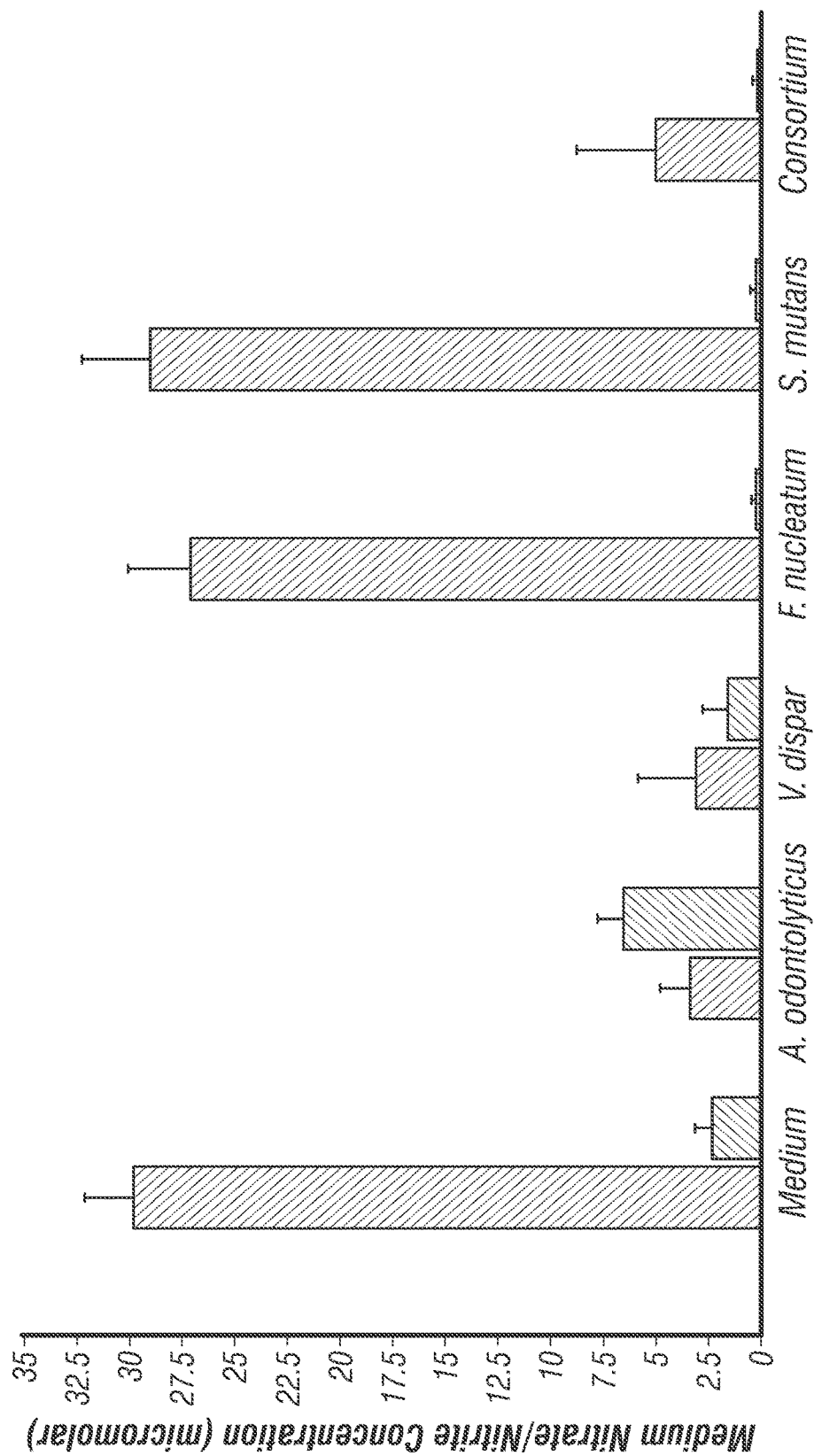
FIG. 3: The nitrate- and nitrite-reducing capacity of four candidate species grown individually and as a consortium. Each bar represents the concentration of nitrate and nitrite remaining in the spent medium after 24 hours of incubation for anaerobic biofilms consisting of individual species (*A. odontolyticus, V. dispar, F. nucleatum*, and *S. mutans*) or a consortium of all four species at 24 hours after biofilm inoculation. The nitrate concentration is indicated by the left-hand bar for each sample and is shown in light gray. The nitrite concentration is indicated by the right-hand bar for each sample and is shown in dark gray. The data are the average±SEM of three individual experiments.

Biochemical characterization of nitrate and nitrite reduction by four species identified through WGS analysis: To begin to assess the nitrate and nitrite reduction by the candidate species identified through metagenomics analyses of the human tongue scrapings, the in vitro nitrate- and nitrite-reducing capacities of recent isolates of four representative species were examined. *Actinomyces odontolyticus, Fusobacterium nucleatum*, and *Veillonella dispar*, along with *Streptococcus mutans* as a representative of bacteria associated with poor oral health. *A. odontolyticus* represents candidate taxa that possess only nitrate-reductase encoding genes in their genomes, *V. dispar* represents taxa that possess both nitrate- and nitrite-reductase encoding genes, and *F. nucleatum* represents taxa that possess only nitrite-reductase encoding genes. Additionally *S. mutans* also possesses only nitrite-reducing encoding genes. The strains were grown individually and as a consortium of all four strains using the same in vitro biofilm protocol used to grow the original tongue-scraping samples. The apparent nitrate- and nitrite-reduction activities of the species were inferred from the amount of nitrate and nitrite remaining in the spent medium (FIG. 3). As expected, both *A. odontolyticus* and *V. dispar* were effective nitrate reducers, reducing at least 80% of medium nitrate. In contrast, *S. mutans* and *F. nucleatum* did not reduce nitrate, although there were almost undetectable levels of nitrite remaining in the media of these biofilms. *V. dispar* also reduced nitrite, but not to the extent of either *S. mutans* or *F. nucleatum*. The sequenced strains of *A. odontolyticus* do not possess a nitrite-reductase gene, and nitrite levels increased in the medium of the *A. odontolyticus* biofilm compared to fresh, sterile medium, confirming that the isolated strain also does not possess a functional nitrite reductase and supporting the designation of *A. odontolyticus* as a top candidate for nitrate reduction and nitrite accumulation.

The consortium of all four species exhibited good nitrate and nitrite reduction, as the nitrate levels in the spent medium were low and the nitrite levels were undetectable. However, nitrate levels were not any lower than those detected in the medium of either the *A. odontolyticus* or *V. dispar* biofilms alone, and it appeared that any nitrite released into the medium was quickly reduced by *S. mutans* and *F. nucleatum*. These data corroborate the metagenomic identification and the functional activity of these bacteria demonstrating that this approach can be useful for screening for specific bacteria.

Through the above tests, an in-depth view was achieved of the differences between microbial biofilm communities that are good, fair, and poor at reducing nitrate. This allowed the identification of species that likely contribute to optimal nitrate reduction in the human host to provide the human body with continuous sources of nitrite and NO. The optimal community would reduce the maximum amount of nitrate, while also allowing nitrite accumulation, such as was observed in the *Actinomyces odontolyticus* biofilm, to maximize the amount of bioactive nitrite available in the saliva of the host. Current theory suggests that although some members of the oral microbiome reduce nitrite, it is a slow reaction and is not generally accounted for, as the rate of nitrate reduction is fast and coupled to rapid extrusion of nitrite (Doel, Benjamin et al. 2005). In contrast to this view, in our multi-species biofilm conditions, no nitrite was detected in the spent medium; however, this was a closed system, while the oral cavity is an open system in which nitrite has the means to be carried away from nitrite-reducing bacteria. Presence of these bacteria may not allow for sufficient nitrite accumulation in the saliva thereby suppressing the nitrate-nitrite-nitric oxide pathway.

The claims are not to be interpreted as including means-plus- or step-plus-function limitations, unless such a limitation is explicitly recited in a given claim using the phrase(s) "means for" or "step for," respectively.

REFERENCES

Abubucker, S., N. Segata, et al. (2012). "Metabolic reconstruction for metagenomic data and its application to the human microbiome." *PLoS Comput Biol* 8(6): e1002358.

Bryan, N. S., J. W. Calvert, et al. (2007). "Dietary nitrite supplementation protects against myocardial ischemia-reperfusion injury." *Proc Natl Acad Sci USA* 104(48): 19144 19149.

Bryan, N. S., J. W. Calvert, et al. (2008). "Dietary nitrite restores NO homeostasis and is cardioprotective in endothelial nitric oxide synthase-deficient mice." *Free Radic Biol Med* 45(4): 468-474.

Bryan, N. S. and M. B. Grisham (2007). "Methods to detect nitric oxide and its metabolites in biological samples." *Free Radic Biol Med* 43(5): 645-657.

Bugiardini, R., O. Manfrini, et al. (2004). "Endothelial function predicts future development of coronary artery disease: a study of women with chest pain and normal coronary angiograms." *Circulation* 109(21): 2518-2523.

Caporaso, J. G., J. Kuczynski, et al. (2010). "QIIME allows analysis of high-throughput community sequencing data." *Nat Methods* 7(5): 335-336.

Carlstrom, M., F. J. Larsen, et al. (2010). "Dietary inorganic nitrate reverses features of metabolic syndrome in endothelial nitric oxide synthase-deficient mice." *PNAS* 107(41): 17716-17720.

Carlstrom, M., A. E. Persson, et al. (2011). "Dietary nitrate attenuates oxidative stress, prevents cardiac and renal injuries, and reduces blood pressure in salt-induced hypertension." *Cardiovascular Research* 89(3): 574-585.

Consortium, T. H. M. P. (2012). "Structure, function and diversity of the healthy human microbiome." *Nature* 486 (7402): 207-214.

Dewhirst, F. E., T. Chen, et al. (2010). "The human oral microbiome." *J Bacteriol* 192(19): 5002 5017.

Doel, J., N. Benjamin, et al. (2005). "Evaluation of bacterial nitrate reduction in the human oral cavity." *European Journal of Oral Sciences* 113: 14-19.

Duncan, C., H. Dougall, et al. (1995). "Chemical generation of nitric oxide in the mouth from the enterosalivary circulation of dietary nitrate." *Nature Medicine* 1(6): 546-551.

Gitaitis, (1987): "Refinement of Lyophilization Methodology for Storage of Large Numbers of Bacterial Strains" *Plant Disease,* 71: 615-616.

Guergoletto et al. (2012). "Dried Probiotics for Use in Functional Food Applications—Methods and Equipment," ISBN: 978-953-307-905-9, InTech, Available from: http://www.intechopen.com/books/food-industrialprocesses-methods-and-equipment/dried-probiotics-for-use-in-functional-food-applications.

Halcox, J. P. J. (2002). "Prognostic Value of Coronary Vascular Endothelial Dysfunction." *Circulation* 106(6): 653-658.

Hendgen-Cotta, U. B., P. Luedike, et al. (2012). "Dietary nitrate supplementation improves revascularization in chronic ischemia." *Circulation* 126(16): 1983-1992.

Joshipura, K., C. Ritchie, et al. (2000). "Strength of evidence linking oral conditions and systemic disease." *Compend Contin Educ Dent Suppl*(30): 12-23; quiz 65.

Kapil, V., S. M. Haydar, et al. (2013). "Physiological role for nitrate-reducing oral bacteria in blood pressure control." *Free Radic Biol Med* 55: 93-100.

Kleinbongard, P., A. Dejam, et al. (2006). "Plasma nitrite concentrations reflect the degree of endothelial dysfunction in humans." *Free Radic Biol Med* 40(2): 295-302.

Lerman, A. and A. M. Zeiher (2005). "Endothelial function: cardiac events." *Circulation* 111(3): 363-368.

Lundberg, J., E. Weitzberg, et al. (2004). "Nitrate, bacteria, and human health." *Nature Reviews Microbiology* 2: 593-602.

Lundberg, J. O. and M. Govoni (2004). "Inorganic nitrate is a possible source for systemic generation of nitric oxide." *Free Radic Biol Med* 37(3): 395-400.

Lundberg, J. O., E. Weitzberg, et al. (2004). "Nitrate, bacteria and human health." *Nat Rev Microbiol* 2(7): 593-602.

Lundberg, J. O., E. Weitzberg, et al. (2008). "The nitrate-nitrite-nitric oxide pathway in physiology and therapeutics." *Nat Rev Drug Discov* 7(8): 156-167

Moncada, S. and A. Higgs (1993). "The L-Arginine-Nitric Oxide Pathway." *The New England Journal of Medicine* 329(27): 2002-2012.

Moncada, S., R. M. J. Palmer, et al. (1991). "Nitric oxide: physiology, pathophysiology and pharmacology." *Pharmacol Rev* 43(2): 109-142.

Petersson, J., M. Carlstrom, et al. (2009). "Gastroprotective and blood pressure lowering effects of dietary nitrate are abolished by an antiseptic mouthwash." *Free Radic Biol Med* 46(8): 1068-1075.

Robles Alonso, V. and F. Guarner (2013). "Linking the gut microbiota to human health." *Br J Nutr* 109 Suppl 2: S21-26.

Schachinger, V., M. B. Britten, et al. (2000). "Prognostic impact of coronary vasodilator dysfunction on adverse long-term outcome of coronary heart disease." *Circulation* 101 (16): 1899-1906.

Segata, N., L. Waldron, et al. (2012). "Metagenomic microbial community profiling using unique clade-specific marker genes." *Nat Methods* 9(8): 811-814.

Stackebrandt, E., D. Witt, et al. (1991). "Designation of Streptomycete 16S and 23S rRNA-based target regions for oligonucleotide probes." *Appl Environ Microbiol* 57(5): 1468 1477.

Webb, A., R. Bond, et al. (2004). "Reduction of nitrite to nitric oxide during ischemia protects against myocardial ischemia-reperfusion damage." *Proc Natl Acad Sci USA* 101(13683 13688).

Webb, A. J., N. Patel, et al. (2008). "Acute blood pressure lowering, vasoprotective, and antiplatelet properties of dietary nitrate via bioconversion to nitrite." *Hypertension* 51(3): 784-790.

Yeboah, J., J. R. Crouse, et al. (2007). "Brachial flow-mediated dilation predicts incident cardiovascular events in older adults: the Cardiovascular Health Study." *Circulation* 115(18): 2390-2397.

Yeboah, J., A. R. Folsom, et al. (2009). "Predictive value of brachial flow-mediated dilation for incident cardiovascular events in a population-based study: the multi-ethnic study of atherosclerosis." *Circulation* 120(6): 502-509.

The invention claimed is:

1. A method of establishing or enhancing a bacteria population in the oral cavity of an individual comprising administering to the individual a probiotic composition, where the probiotic composition consists of bacteria of *Neisseria, Haemophilus, Prevotella,* and *Leptotrichia,* where the composition is in the form of tablet, a capsule, a granule powder, a gum, a biofilm, an oral liquid preparation, a food-product serving, or a lozenge.

2. The method of claim 1, wherein the bacteria consists essentially of strains that contain nitrate-reductase encoding genes and do not contain nitrite-reductase encoding genes.

3. The method of claim 1, wherein the bacteria consists essentially of strains that express one or more of the following nitrate reductase genes: narG, narL, narJ, narQ, nail, napC, napB, napH, napD, napA, napG, and napF.

4. The method of claim 1, wherein the bacteria consists essentially of strains that do not express the following nitrite reductase genes: nirK, nirB, nirD, nrfF, nrfA, and nrfH.

5. The method of claim 1, wherein the bacteria consists essentially of strains that do not express nitric oxide reductase.

6. The method of claim 1, wherein the bacteria consists essentially of weak acid or non-acid producing bacterial strains.

7. The method of claim 1, wherein a dosage of the composition comprises 1 mg to 100 g of the bacteria.

8. The method of claim 1, where a dosage of the composition comprise an activity of 5 billion to 20 billion colony forming units.

9. The method of claim 1, wherein the probiotic composition is stored at or below 45° C. or wherein the bacteria are freeze-dried.

10. The method of claim 1, wherein the bacteria are genetically-modified or recombinant bacteria, where a gene encoding nitric oxide reductase is suppressed.

11. The method of claim 1, wherein the probiotic composition further comprises nitrate.

12. The method of claim 1, wherein the probiotic composition further comprises a botanical source of nitrate and the botanical source of nitrate comprises one or more of beet root, kale, artichoke, holy basil, gymnema sylvestre, ashwagandha root, salvia, St. John wort, broccoli, stevia, spinach, gingko, kelp, tribulus, eleuthero, epimedium, eucommia, hawthorn berry, rhodiola, green tea, codonopsys, panax ginseng, astragalus, pine bark, dodder seed, Schisandra, cordyceps, and mixtures thereof.

13. The method of claim 1, the probiotic composition further comprises the one or more excipients, wherein the one or more excipients comprises a substance having a pH buffering capacity, wherein the pH buffering substance is selected from the group consisting of bicarbonates, carbamides, phosphates, proteins, salts, and combinations of two or more thereof.

14. The method of claim 1, wherein the composition is administered to subjects suffering from one or more of cardiovascular disease, atherosclerosis, stroke, ischemic injury, peripheral artery disease, congestive heart failure, hypertension, pulmonary arterial hypertension, hypertension associated with urea cycle disorders and pre-eclampsia, vascular dementia, Alzheimer's Disease, metabolic syndrome, and type 2 diabetes.

* * * * *